US012789188B2

(12) United States Patent
Brown et al.

(10) Patent No.: US 12,789,188 B2
(45) Date of Patent: Nov. 10, 2026

(54) FLOW CELLS WITH DARK QUENCHER

(71) Applicant: ILLUMINA, INC., San Diego, CA (US)

(72) Inventors: Andrew A. Brown, Cambridge (GB); Wayne N. George, Ilford (GB)

(73) Assignee: Illumina, Inc., San Diego, CA (US)

( * ) Notice: Subject to any disclaimer, the term of this patent is extended or adjusted under 35 U.S.C. 154(b) by 737 days.

(21) Appl. No.: 17/936,200

(22) Filed: Sep. 28, 2022

(65) Prior Publication Data

US 2023/0101095 A1 Mar. 30, 2023

Related U.S. Application Data

(60) Provisional application No. 63/249,841, filed on Sep. 29, 2021.

(51) Int. Cl.

| | |
|---|---|
| ***B01L 3/00*** | (2006.01) |
| ***C08L 33/26*** | (2006.01) |
| ***C12Q 1/6874*** | (2018.01) |
| ***G01N 21/64*** | (2006.01) |

(52) U.S. Cl.

CPC ......... *B01L 3/502761* (2013.01); *C08L 33/26* (2013.01); *C12Q 1/6874* (2013.01); *G01N 21/6428* (2013.01); *B01L 2200/0647* (2013.01); *B01L 2300/0654* (2013.01); *G01N 2021/6439* (2013.01)

(58) Field of Classification Search

None

See application file for complete search history.

(56) References Cited

U.S. PATENT DOCUMENTS

| | | | | |
|---|---|---|---|---|
| 10,106,839 | B2 | 10/2018 | Hassibi | |
| 10,378,051 | B2 | 8/2019 | Meuleman et al. | |
| 2010/0312483 | A1* | 12/2010 | Peyser | G01N 33/52 702/19 |
| 2015/0218625 | A1 | 8/2015 | Rice et al. | |
| 2016/0146799 | A1 | 5/2016 | Robinson et al. | |
| 2016/0243254 | A1 | 8/2016 | Artzi et al. | |
| 2020/0024661 | A1* | 1/2020 | Merkel | C09D 153/00 |

FOREIGN PATENT DOCUMENTS

| | | | | |
|---|---|---|---|---|
| CN | 107110851 B | | 10/2019 | |
| CN | 107569448 B | | 8/2020 | |
| EP | 1173878 B1 | | 4/2011 | |
| WO | 2000066265 A2 | | 11/2000 | |
| WO | 2009056831 A1 | | 5/2009 | |
| WO | WO-2010111674 A2 | * | 9/2010 | C07H 19/20 |
| WO | WO-2017007838 A1 | * | 1/2017 | B01J 19/0046 |
| WO | WO-2021126503 A1 | * | 6/2021 | C12Q 1/6848 |

OTHER PUBLICATIONS

Le Reste et al., "Characterization of Dark Quencher Chromophones as Nonfluorescent Acceptors for Single-Molecule FRET", Biophysical Journal, vol. 102, No. 11, Apr. 6, 2012 (Apr. 6, 2012), pp. 2658-2668, doi:10.1016/j.bpj.2012.04.028, Apr. 6, 2012.

* cited by examiner

*Primary Examiner* — Matthew D Krcha

(74) *Attorney, Agent, or Firm* — Dierker & Kavanaugh, P.C.

(57) ABSTRACT

An example flow cell includes a substrate having a surface. The flow cell also includes a polymeric hydrogel attached to at least a portion of the substrate surface, where the polymeric hydrogel includes a dark quencher. The flow cell further includes at least one primer set attached to the polymeric hydrogel.

16 Claims, 6 Drawing Sheets

Specification includes a Sequence Listing.

SEQUENCE LISTING

```
Sequence total quantity: 19
SEQ ID NO: 1            moltype = DNA  length = 29
FEATURE                 Location/Qualifiers
source                  1..29
                        mol_type = other DNA
```

-continued

```
                         organism = synthetic construct
modified_base            23
                         mod_base = OTHER
                         note = uracil
SEQUENCE: 1
aatgatacgg cgaccaccga gatctacac                                   29

SEQ ID NO: 2             moltype = DNA  length = 24
FEATURE                  Location/Qualifiers
source                   1..24
                         mol_type = other DNA
                         organism = synthetic construct
misc_difference          22
                         note = 8-oxoguanine
SEQUENCE: 2
caagcagaag acggcatacg anat                                        24

SEQ ID NO: 3             moltype = DNA  length = 24
FEATURE                  Location/Qualifiers
source                   1..24
                         mol_type = other DNA
                         organism = synthetic construct
misc_difference          20
                         note = 8-oxoguanine
SEQUENCE: 3
caagcagaag acggcatacn agat                                        24

SEQ ID NO: 4             moltype = DNA  length = 29
FEATURE                  Location/Qualifiers
source                   1..29
                         mol_type = other DNA
                         organism = synthetic construct
misc_difference          23
                         note = allyl-T
SEQUENCE: 4
aatgatacgg cgaccaccga ganctacac                                   29

SEQ ID NO: 5             moltype = DNA  length = 35
FEATURE                  Location/Qualifiers
source                   1..35
                         mol_type = other DNA
                         organism = synthetic construct
SEQUENCE: 5
gctggcacgt ccgaacgctt cgttaatccg ttgag                            35

SEQ ID NO: 6             moltype = DNA  length = 35
FEATURE                  Location/Qualifiers
source                   1..35
                         mol_type = other DNA
                         organism = synthetic construct
SEQUENCE: 6
cgtcgtctgc catggcgctt cggtggatat gaact                            35

SEQ ID NO: 7             moltype = DNA  length = 35
FEATURE                  Location/Qualifiers
source                   1..35
                         mol_type = other DNA
                         organism = synthetic construct
SEQUENCE: 7
acggccgcta atatcaacgc gtcgaatccg caact                            35

SEQ ID NO: 8             moltype = DNA  length = 34
FEATURE                  Location/Qualifiers
source                   1..34
                         mol_type = other DNA
                         organism = synthetic construct
SEQUENCE: 8
gccgcgttac gttagccgga ctattcgatg cagc                             34

SEQ ID NO: 9             moltype = DNA  length = 24
FEATURE                  Location/Qualifiers
source                   1..24
                         mol_type = other DNA
                         organism = synthetic construct
SEQUENCE: 9
aggaggagga ggaggaggag gagg                                        24

SEQ ID NO: 10            moltype = DNA  length = 24
FEATURE                  Location/Qualifiers
```

-continued

```
source                1..24
                      mol_type = other DNA
                      organism = synthetic construct
SEQUENCE: 10
cctcctcctc ctcctcctcc tcct                                          24

SEQ ID NO: 11         moltype =   length =
SEQUENCE: 11
000

SEQ ID NO: 12         moltype =   length =
SEQUENCE: 12
000

SEQ ID NO: 13         moltype =   length =
SEQUENCE: 13
000

SEQ ID NO: 14         moltype =   length =
SEQUENCE: 14
000

SEQ ID NO: 15         moltype = DNA  length = 29
FEATURE               Location/Qualifiers
source                1..29
                      mol_type = other DNA
                      organism = synthetic construct
modified_base         23
                      mod_base = OTHER
                      note = uracil
misc_feature          27
                      note =
                       4'-(2-nitro-4-toluyldiazo)-2'-methoxy-5'-methyl-azobenzene-
                       4''-(N-ethyl)-N-ethyl-2-cyanoethyl-(N,N-diisopropyl)-phosph
                       oramidite
SEQUENCE: 15
aatgatacgg cgaccaccga gatctanac                                     29

SEQ ID NO: 16         moltype = DNA  length = 29
FEATURE               Location/Qualifiers
source                1..29
                      mol_type = other DNA
                      organism = synthetic construct
modified_base         23
                      mod_base = OTHER
                      note = uracil
misc_feature          27
                      note =
                       4'-(4-nitro-phenyldiazo)-2'-methoxy-5'-methoxy-azobenzene-4
                       ''-(N-ethyl)-N-ethyl-2-cyanoethyl-(N,N-diisopropyl)-phospho
                       ramidite
SEQUENCE: 16
aatgatacgg cgaccaccga gatctanac                                     29

SEQ ID NO: 17         moltype = DNA  length = 25
FEATURE               Location/Qualifiers
source                1..25
                      mol_type = other DNA
                      organism = synthetic construct
misc_difference       22
                      note = 8-oxoguanine
misc_feature          25
                      note = ALEXA FLUOR 647
SEQUENCE: 17
caagcagaag acggcatacg anatn                                         25

SEQ ID NO: 18         moltype = DNA  length = 28
FEATURE               Location/Qualifiers
source                1..28
                      mol_type = other DNA
                      organism = synthetic construct
misc_feature          26
                      note =
                       4'-(2-nitro-4-toluyldiazo)-2'-methoxy-5'-methyl-azobenzene-
                       4''-(N-ethyl)-N-ethyl-2-cyanoethyl-(N,N-diisopropyl)-phosph
                       oramidite
SEQUENCE: 18
aatgatacgg cgaccaccga gactanac                                      28
```

-continued

```
SEQ ID NO: 19           moltype = DNA  length = 28
FEATURE                 Location/Qualifiers
source                  1..28
                        mol_type = other DNA
                        organism = synthetic construct
misc_feature            26
                        note =
                         4'-(4-nitro-phenyldiazo)-2'-methoxy-5'-methoxy-azobenzene-4
                         ''-(N-ethyl)-N-ethyl-2-cyanoethyl-(N,N-diisopropyl)-phospho
                         ramidite
SEQUENCE: 19
aatgatacgg cgaccaccga gactanac                                  28
```

FLOW CELLS WITH DARK QUENCHER

CROSS REFERENCE TO RELATED APPLICATION

This application claims the benefit of U.S. Provisional Application Ser. No. 63/249,841 filed Sep. 29, 2021, the contents of which is incorporated by reference herein in its entirety.

REFERENCE TO SEQUENCE LISTING

The Sequence Listing submitted herewith is hereby incorporated by reference in its entirety. The name of the file is ILI223B_IP-2207-US_Sequence_Listing.xml, the size of the file is 20.670 bytes, and the date of creation of the file is Sep. 26, 2022.

BACKGROUND

Many biological sensing and amplification methods utilize fluorescence-based technology. For example, sequencing-by-synthesis methods of genetic sequencing employ fluorescent signals in their operation. More specifically, in a sequencing-by-synthesis approach, a nascent strand is synthesized, and the addition of each monomer (e.g., nucleotide) to the growing strand is detected optically via an emission of a fluorescent signal from an attached fluorophore. Because a template strand directs synthesis of the nascent strand, one can infer the sequence of the template DNA from the series of nucleotide monomers that were added to the growing strand during the synthesis.

SUMMARY

Disclosed herein is a flow cell including a substrate and a polymeric hydrogel including a dark quencher. During sequencing, non-specifically bound fully functional nucleotides (e.g., which include fluorophores) may contribute background noise to a sequencing read. Non-specifically bound fully functional nucleotides are those nucleotides that do not become incorporated into the nascent strand, but rather become trapped at the polymeric hydrogel surface or are free in solution at the polymeric hydrogel surface. Signals from the non-specifically bound fully functional nucleotides can deleteriously interfere with signals from the incorporated fully functional nucleotides, rendering the latter signals difficult to readily resolve. The inclusion of the dark quencher can at least reduce the background signals and thus the background intensity. A reduction in the background intensity increases the signal-to-noise ratio (SNR), which enables the incorporated fully functional nucleotide signals to be readily resolved.

The polymeric hydrogel and the dark quencher described herein may also be used in any sensor that utilizes fluorescence as a detection mechanism (a polymerase chain reaction sensor (PCR), other biological sensors, or the like). In some of the examples disclosed herein, the polymeric hydrogel and the dark quencher are used as a security feature, e.g., to ensure that a sensor is being used in conjunction with the proper analysis system.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
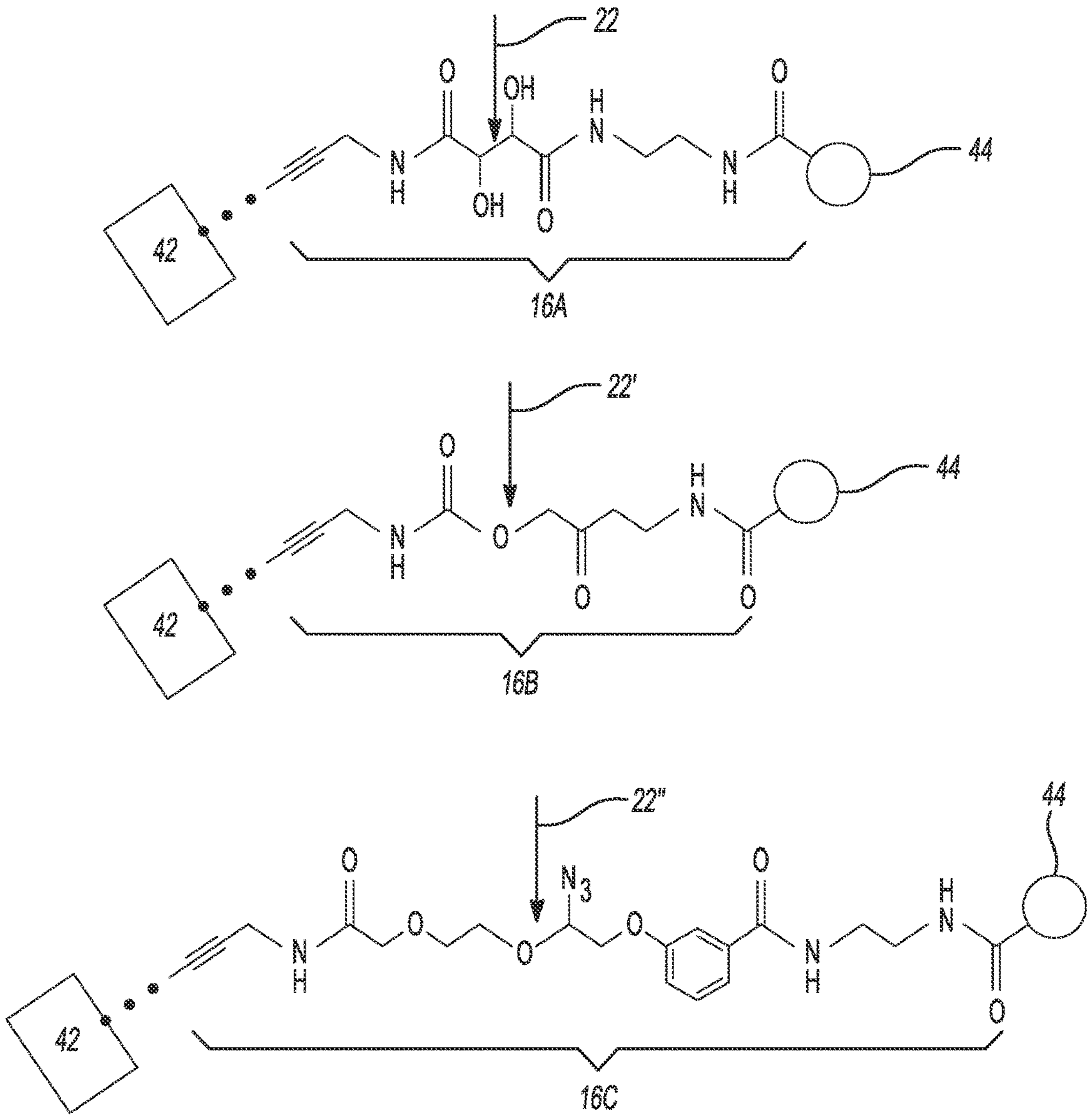
FIG. 1 depicts schematic illustrations of the chemical structures of different examples of cleavable linking molecules attaching a dark quencher to a polymeric hydrogel.

Examples of the flow cell and other fluorescent sensors disclosed herein include a polymeric hydrogel that includes a dark quencher. The inclusion of the dark quencher can at least reduce background signals, and thus the background intensity, resulting from molecules of interest that contain a fluorophore and that are non-specifically bound at the surface of the polymeric hydrogel. Non-specifically bound molecules of interest may be trapped at, or in solution near the surface of the polymeric hydrogel rather than becoming incorporated into nascent strands or otherwise sequestered by a capture substance. In the various examples set forth herein, the dark quencher is positioned within "signal quenching proximity" of the non-specifically bound molecules of interest. By "signal quenching proximity," it is meant that the dark quencher and the non-specifically bound molecules of interest are close enough to each other (e.g., within 4 nm or less for some dark quenchers and optically active molecule(s) of interest) that the background signal(s) from these molecules is/are quenched. Quenching the background signals increases the signal-to-noise ratio (SNR), which enables signals of the incorporated or otherwise sequestered molecules of interest to be readily resolved. As one example, lower background noise enables bases to be called more accurately, which in turn enables longer sequencing runs.

Definitions

It is to be understood that the terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

As used herein, the term "flow cell" is intended to mean a vessel having a flow channel where a reaction can be carried out, an inlet for delivering reagent(s) to the flow channel, and an outlet for removing reagent(s) from the flow channel. In some examples, the flow cell accommodates the detection of a reaction that occurs in the flow cell. For example, the flow cell can include one or more transparent surfaces allowing for the optical detection of arrays, optically labeled molecules, or the like.

As used herein, a "flow channel" or "channel" may be an area defined between two bonded components that can selectively receive a liquid sample. In some examples, the flow channel may be defined between two patterned structures, and thus may be in fluid communication with a surface chemistry of the patterned structures. In other examples, the flow channel may be defined between a patterned structure and a lid, and thus may be in fluid communication with the surface chemistry of the patterned structure.

A "patterned structure" may refer to a single layer substrate, or a multi-layer substrate including a base support and a resin layer positioned on the base support. The single layer substrate or the resin layer of a multi-layer substrate may have surface chemistry in a pattern, e.g., in depressions, or otherwise positioned on the single layer substrate or the resin layer of the multi-layer substrate. The surface chemistry may have a polymeric hydrogel and primers of at least one primer set (e.g., used for library template capture and amplification) attached thereto. In some examples, the single layer substrate or the multi-layer substrate has been exposed to patterning techniques (e.g., etching, lithography, etc.) in order to generate the pattern for the surface chemistry. However, the term "patterned structure" is not intended to imply that such patterning techniques have to be used to generate the pattern. For example, the patterned structure may be a substantially flat surface having a pattern of a polymeric hydrogel thereon.

The term "substrate" refers to a single layer base support or a multi-layer structure including a base support with a resin layer thereon, upon which surface chemistry may be introduced.

As used herein, a "polymeric hydrogel", or a "polymeric hydrogel pad", or a "hydrogel pad", or a "pad" refers to includes any gel (e.g., hydrogel) material that can swell when liquid is taken up and can contract when liquid is removed, e.g., by drying. The polymeric hydrogel may be applied over at least a portion of a flow cell substrate. The polymeric hydrogel may include functional group(s) that can attach to primer(s) or primer sets. The polymeric hydrogel may be applied as a pad, or positioned within a portion of a depression defined in the substrate, or positioned within a portion of a lane defined in the substrate. The polymeric hydrogel pad rests on, and thus appears to protrude from, a substantially flat substrate surface. It is to be understood that "hydrogel pad", "polymeric hydrogel pad", "polymeric pad", and "pad" are used interchangeably herein. The polymeric hydrogel may include a dark quencher removably attached through a cleavable linking molecule, or incorporated into its backbone chain, or covalently attached through a linking molecule, or non-covalently attached through a non-covalent binding pair.

As used herein, a "primer" is defined as a single stranded nucleic acid sequence (e.g., single stranded DNA). Some primers, referred to herein as amplification primers, serve as a starting point for template amplification and cluster generation. Other primers, referred to herein as sequencing primers, serve as a starting point for DNA synthesis. The 5' terminus of the primer may be modified to facilitate a coupling reaction with a functional group of a polymer. The primer length can be any number of bases long and can include a variety of non-natural nucleotides. In an example, the sequencing primer is a short strand, ranging from 10 to 60 bases, or from 20 to 40 bases.

As used herein, a "nucleotide" includes a nitrogen-containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to the N-1 atom of a pyrimidine or the N-9 atom of a purine. The nucleotide may be a monophosphate, or a polyphosphate including several phosphate groups (e.g., tri-phosphate (i.e., gamma phosphate), tetra-phosphate, penta-phosphate, hexa-phosphate, etc.). A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA), phosphonate modified nucleotides in place of the phosphate backbone, etc.

As also used herein, a "fully functional nucleotide" refers to a nucleotide that has at least one fluorophore attached thereto. Incorporated fully functional nucleotides are those nucleotides that have hydrogen bonded to a template strand. Non-specifically bound fully functional nucleotides are those nucleotides that do not become incorporated into the nascent strand, but rather become bound to the polymeric hydrogel.

The term "dark quencher" refers to a non-fluorescent dye that absorbs emission energy (light) from a fluorophore and subsequently dissipates the absorbed energy as heat rather than as a fluorescent signal.

A "signal-to-noise ratio" refers to a ratio of an amount of a target fluorescent signal detected during a sequencing method to an amount of background fluorescence detected during the sequencing method.

The term "background fluorescence" or "noise" refers to signals produced by non-target sources, which may be contributed by non-specifically bound fully functional nucleotides trapped at a surface of a polymeric hydrogel or in solution near the hydrogel surface. The term "background fluorescence" may also encapsulate undesired signals produced by the substrate, e.g., the resin layer of a multi-layer substrate.

The term "cleavable linking molecule" refers to a molecule that reacts with an enzyme or other reactant to cleave, or cut away, a portion of the molecule and thereby excise a particular functional group from the molecule's overall structure.

An "acrylamide monomer" is a monomer with the structure

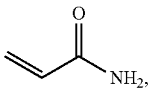

or a monomer including an acrylamide group. Examples of the monomer including an acrylamide group include azido acetamido pentyl acrylamide:

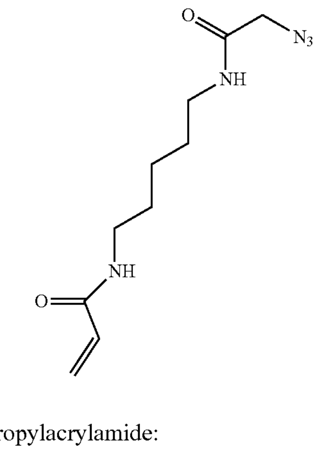

and N-isopropylacrylamide:

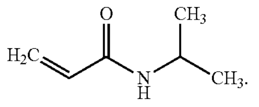

Other acrylamide monomers may be used.

As used herein, a "capture substance" refers to a material attached to a portion of a flow cell surface or attached to a portion of a fluorescent sensor surface that attaches a molecule of interest (e.g., a library fragment, an analyte, etc.). In the flow cells described herein, primers or primer sets function as the capture substance. In other sensors, the capture substance may be PCR primers, receptors, etc.

As used herein, the term "depression" refers to a discrete concave feature in a substrate surface, the feature having a surface opening that is at least partially surrounded by interstitial region(s) of the substrate surface. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

As used herein, the term "interstitial region" refers to an area, e.g., of a substrate surface that separates depressions (concave regions). For example, an interstitial region can separate one depression of an array from another depression of the array. The two depressions that are separated from each other can be discrete, i.e., lacking physical contact with each other. In many examples, the interstitial region is continuous, whereas the depressions are discrete, for example, as is the case for a plurality of depressions defined in an otherwise continuous surface. In other examples, the interstitial regions and the features are discrete, for example, as is the case for a plurality of depressions in the shape of trenches, which are separated by respective interstitial regions. Separation provided by an interstitial region can be partial or full separation. Interstitial regions may have a surface material that differs from the surface material of the depressions. For example, depressions can have a polymeric hydrogel and primer set(s) attached therein, and the interstitial regions can be free of polymeric hydrogel and primer set(s).

As used herein, the term "attached" refers to the state of two things being joined, fastened, adhered, connected or bound to each other, either directly or indirectly. For example, a nucleic acid can be attached to a polymeric hydrogel by a covalent or non-covalent bond. A "covalent bond" is characterized by the sharing of pairs of electrons between atoms. A "non-covalent bond" is a physical bond that does not involve the sharing of pairs of electrons and can include, for example, hydrogen bonds, ionic bonds, van der Waals forces, hydrophilic interactions and hydrophobic interactions.

The terms top, bottom, lower, upper, on, etc. are used herein to describe the flow cell or other fluorescent sensor and/or the various components of the flow cell or other fluorescent sensor. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

The term "activation," as used herein, refers to a process that generates reactive groups at the surface of the single layer base support or an outermost layer of the multi-layered substrate. Activation may be accomplished using silanization or plasma ashing. While the figures do not depict a separate silanized layer or —OH groups from plasma ashing, it is to be understood that activation generates a silanized layer or —OH groups at the surface of the activated support or layer to covalently attach the polymeric hydrogel to the underlying support or layer.

An aldehyde, as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

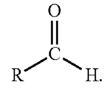

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amine" or "amino" functional group refers to an $—NR_aR_b$ group, where $R_a$ and $R_b$ are each independently selected from hydrogen (e.g., 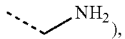), C1-6 alkyl, C2-6 alkenyl, C2-6 alkynyl, C3-7 carbocycle, C6-10 aryl, 5-10 membered heteroaryl, and 5-10 membered heterocycle, as defined herein.

An "azide" or "azido" functional group refers to $—N_3$.

As used herein, "carbocycle" means a non-aromatic cyclic ring or ring system containing only carbon atoms in the ring system backbone. When the carbocycle is a ring system, two or more rings may be joined together in a fused, bridged or spiro-connected fashion. Carbocycles may have any degree of saturation, provided that at least one ring in a ring system is not aromatic. Thus, carbocycles include cycloalkyls, cycloalkenyls, and cycloalkynyls. The carbocycle group may have 3 to 20 carbon atoms. Examples of carbocycle rings include cyclopropyl, cyclobutyl, cyclopentyl, cyclohexyl, cyclohexenyl, 2,3-dihydro-indene, bicyclo [2.2.2]octanyl, adamantyl, and spiro[4.4]nonanyl.

As used herein, the term "carboxylic acid" or "carboxyl" refers to —COOH.

As used herein, "cycloalkylene" means a fully saturated carbocycle ring or ring system that is attached to the rest of the molecule via two points of attachment.

As used herein, "cycloalkenyl" or "cycloalkene" means a carbocycle ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocycle ring or ring system with at least one heteroatom in ring backbone, having at least one double bond, wherein no ring in the ring system is aromatic.

As used herein, "cycloalkynyl" or "cycloalkyne" means a carbocycle ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocycle ring or ring system with at least one heteroatom in ring backbone, having at least one triple bond, wherein no ring in the ring system is aromatic.

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

The term "each," when used in reference to a collection of items, is intended to identify an individual item in the collection, but does not necessarily refer to every item in the collection. Exceptions can occur if explicit disclosure or context clearly dictates otherwise.

The term "epoxy" (also referred to as a glycidyl or oxirane group) as used herein refers to

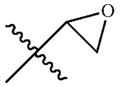

or

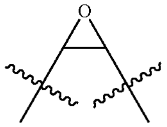

.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocycle" means a non-aromatic cyclic ring or ring system containing at least one heteroatom in the ring backbone. Heterocycles may be joined together in a fused, bridged or spiro-connected fashion. Heterocycle may have any degree of saturation provided that at least one ring in the ring system is not aromatic. In the ring system, the heteroatom(s) may be present in either a non-aromatic or aromatic ring. The heterocycle group may have 3 to 20 ring members (i.e., the number of atoms making up the ring backbone, including carbon atoms and heteroatoms). In some examples, the heteroatom(s) is/are O, N, or S.

The term "hydrazine" or "hydrazinyl" as used herein refers to a $—NHNH_2$ group.

As used herein, the term "hydrazone" or "hydrazonyl" refers to a

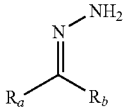

group in which $R_a$ and $R_b$ are each independently selected from hydrogen, C1-6 alkyl, C2-6 alkenyl, C2-6 alkynyl, C3-7 carbocycle, C6-10 aryl, 5-10 membered heteroaryl, and 5-10 membered heterocycle, as defined herein.

As used herein, "hydroxy" or "hydroxyl" refers to an —OH group.

"Nitrile oxide," as used herein, means a "$R_aC≡N^+O^-$" group in which $R_a$ is defined herein. Examples of preparing nitrile oxide include in situ generation from aldoximes by treatment with chloramide-T, or through action of base on imidoyl chlorides [RC(Cl)═NOH], or from the reaction between hydroxylamine and an aldehyde.

"Nitrone," as used herein, means a

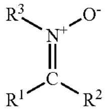

group in which $R^1$, $R^2$, and $R^3$ may be any of the $R_a$ and $R_b$ groups defined herein, except that $R^3$ is not hydrogen (H).

In some examples, the term "over" may mean that one component or material is positioned directly on another component or material. When one is directly on another, the two are in contact with each other.

In other examples, the term "over" may mean that one component or material is positioned indirectly on another component or material. By indirectly on, it is meant that a gap or an additional component or material may be positioned between the two components or materials.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

It is to be understood that the ranges provided herein include the stated range and any value or sub-range within the stated range, as if such values or sub-ranges were explicitly recited. For example, a range of about 400 nm to about 1 μm (1000 nm) should be interpreted to include not only the explicitly recited limits of about 400 nm to about 1 μm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

Polymeric Hydrogel and Dark Quencher

In the examples disclosed herein, the polymeric hydrogel includes the dark quencher. Generally, the polymeric hydrogel has the dark quencher removably attached through a cleavable linking molecule, or the polymeric hydrogel has the dark quencher incorporated into its backbone chain, or the dark quencher is covalently attached to the polymeric hydrogel through a linking molecule. In some examples, the dark quencher may be attached to the polymeric hydrogel through a hairpin oligonucleotide or a DNA origami.

In an example, the polymeric hydrogel includes an acrylamide copolymer. In this example, the acrylamide copolymer has a structure (I):

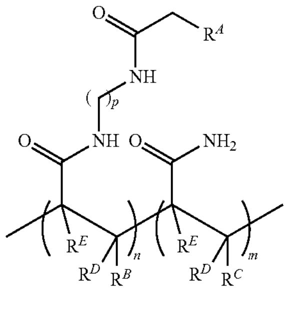

wherein:

- $R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;
- $R^B$ is H or optionally substituted alkyl;
- $R^C$, $R^D$, and $R^E$ are each independently selected from the group consisting of H and optionally substituted alkyl;
- each of the $-(CH_2)_p-$ can be optionally substituted;
- p is an integer in the range of 1 to 50;
- n is an integer in the range of 1 to 50,000; and
- m is an integer in the range of 1 to 100,000.

One specific example of the acrylamide copolymer represented by structure (I) is poly(N-(5-azidoacetamidylpentyl)acrylamide-co-acrylamide, PAZAM.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the acrylamide copolymer may range from about 5 kDa to about 1500 kDa, or from about 10 kDa to about 1000 kDa, or may be, in a specific example, about 312 kDa.

In some examples, the acrylamide copolymer is a linear polymer. In some other examples, the acrylamide copolymer is a lightly cross-linked polymer.

In some examples, the gel material may be a variation of structure (I). In one example, the acrylamide unit may be replaced with N,N-dimethylacrylamide

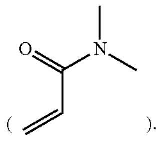

In another example, the acrylamide unit in structure (I) may be replaced with,

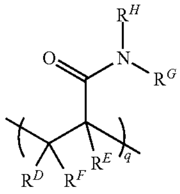

where $R^D$, $R^E$, and $R^F$ are each H or a C1-C6 alkyl, and $R^G$ and RH are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

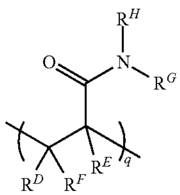

in addition to the recurring "n" and "m" features, where $R^D$, $R^E$, and $R^F$ are each H or a C1-C6 alkyl, and $R^G$ and RH are each a C1-C6 alkyl. In this example, q may be an integer in the range of 1 to 100,000.

As another example of the polymeric hydrogel, the recurring "n" feature in structure (I) may be replaced with a monomer including a heterocyclic azido group having structure (II):

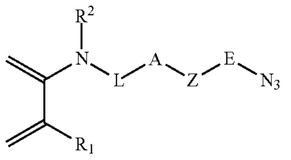

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 carbon-containing ring members present as a single cyclic structure or a fused structure. Some specific examples of Z include pyrrolidinyl, pyridinyl, or pyrimidinyl. As still another example, the gel material may include a recurring unit of each of structure (III) and (IV):

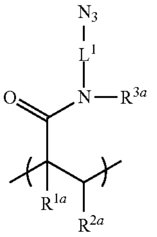

and

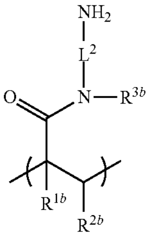

wherein each of $R^{1a}$, $R^{2a}$, $R^{1b}$ and $R^{2b}$ is independently selected from hydrogen, an optionally substituted alkyl or an optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each of $L^1$ and $L^2$ is independently selected from an optionally substituted alkylene linker or an optionally substituted heteroalkylene linker.

In another example, the polymeric hydrogel may be a linear or branched copolymer including a first acrylamide monomer having a structure:

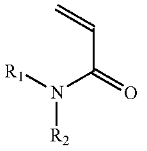

wherein $R^1$ and $R^2$ are independently selected from the group consisting of an alkyl, an alkylamino, an alkylamido, an alkylthio, an aryl, a glycol, and optionally substituted variants thereof; and a second acrylamide monomer having a structure:

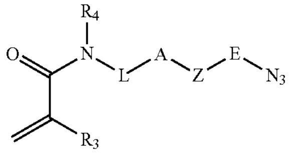

wherein $R^3$ is hydrogen or an alkyl; $R^4$ is hydrogen or an alkyl; L is a linker including a linear chain of 2 atoms to 20 atoms selected from the group consisting of carbon, oxygen, and nitrogen and optional substituents on the carbon and any nitrogen atoms in the chain; A is an N substituted amide having a structure

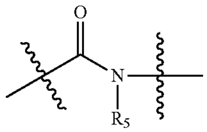

, where $R^5$ is hydrogen or an alkyl; E is a linear chain of 1 atom to 4 atoms selected from the group consisting of carbon, oxygen and nitrogen, and optional substituents on the carbon and any nitrogen atoms in the chain; and Z is an optional nitrogen containing heterocycle.

In still another example, the acrylamide copolymer is formed using nitroxide mediated polymerization, and thus at least some of the copolymer chains have an alkoxyamine end group. In the copolymer chain, the term "alkoxyamine end group" refers to the dormant species $—ONR_1R_2$, where each of $R_1$ and $R_2$ may be the same or different, and may independently be a linear or branched alkyl, or a ring structure, and where the oxygen atom is attached to the rest of the copolymer chain. In some examples, the alkoxyamine may also be introduced into some of the recurring acrylamide monomers, e.g., at position $R^A$ in structure (I). As such, in one example, structure (I) includes an alkoxyamine end group; and in another example, structure (I) includes an alkoxyamine end group and alkoxyamine groups in at least some of the side chains.

It is to be understood that other molecules may be used to form the polymeric hydrogel as long as they are capable of being functionalized with the desired chemistry, e.g., primers. Some examples of suitable materials for the polymeric hydrogel include functionalized silanes, such as norbornene silane, azido silane, alkyne functionalized silane, amine functionalized silane, maleimide silane, or any other silane having functional groups that can respectively attach the desired chemistry.

Still other examples of suitable materials for the polymeric hydrogel include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photocycloaddition reactions. Still other examples of suitable materials for the polymeric hydrogel include mixed copolymers of acrylamides and acrylates. A variety of polymer architectures containing acrylic monomers (e.g., acrylamides, acrylates etc.) may be utilized in the examples disclosed herein, such as branched polymers including dendrimers (e.g., multi-arm or star polymers). For example, the monomers (e.g., acrylamide, etc.) may be incorporated, either randomly or in block, into the branches (arms) of a dendrimer.

As mentioned previously, the polymeric hydrogel disclosed herein includes a dark quencher. Any dark quencher that is capable of being included in the polymeric hydrogel (e.g., in the polymeric hydrogel backbone, attached via a linker, etc.) and is capable of quenching the desired source of fluorescence may be used. The dark quencher may be any black hole quencher, including those in the BHQ® series from Biosearch Technologies, e.g., BHQ® 0 (quenching 430 nm-520 nm), BHQ® 1 (quenching 480 nm-580 nm), BHQ® 2 (quenching 560 nm-670 nm), and BHQ® 3 (quenching 620 nm-730 nm). The emission quenching portion of these molecules (e.g., the substituted rings around the azo system) is available for 3', internal, and/or 5' modifications, which enable polymerizable groups (e.g., acrylamides, acrylates, etc.) or linking molecules to be attached thereto. In an example described herein, the dark quencher is selected from the group consisting of dimethylaminoazobenzenesulfonic acid, 4'-(2-nitro-4-toluyldiazo)-2'-methoxy-5'-methyl-azobenzene-4"-(N-ethyl)-N-ethyl-2-cyanoethyl-(N,N-diisopropyl)-phosphoramidite (i.e., 5'-BHQ-1 Phosphoramidite), 4'-(4-nitro-phenyldiazo)-2'-methoxy-5'-methoxy-azobenzene-4"-(N-ethyl)-N-ethyl-2-cyanoethyl-(N,N-diisopropyl)-phosphoramidite (i.e., 5'-BHQ-2 Phosphoramidite), 5'-Dimethoxytrityloxy-5-[(N-4"-carboxyethyl-4"-(N-ethyl)-4'-(2-Nitro-4-toluyldiazo)-2'-methoxy-5'-methyl-azobenzene)-aminohexyl-3-acrylimido]-2'-deoxyUridine-3'-[(2-cyanoethyl)-(N,N-diisopropyl)]-phosphoramidite (i.e., BHQ-1-dT), 5'-Dimethoxytrityloxy-5-[(N-4"-carboxyethyl-4"-(N-ethyl)-4'-(4-Nitro-phenyldiazo)-2'-methoxy-5'-methoxy-azobenzene)-aminohexyl-3-acrylimido]-2'-deoxyUridine-3'-[(2-cyanoethyl)-(N,N-diisopropyl)]-phosphoramidite (i.e., BHQ-2-dT) and combinations thereof. With these particular examples, dimethylaminoazobenzenesulfonic acid is suitable for use with non-oligonucleotide linking molecules, while the phosphoramidite terminated examples are suitable for use with oligonucleotide linking molecules.

In an example, the polymeric hydrogel has the dark quencher removably attached through a cleavable linking molecule. “Removably attached” means that the dark quencher can be removed from the polymeric hydrogel by a cleaving agent, which cleaves the cleavable linking molecule.

In some examples, the cleavable linking molecule is capable of covalent attachment. Examples of cleavable linking molecules that are capable of covalent attachment are depicted in FIG. 1 at reference numerals 16A, 16B, 16C. In these examples, the cleavable linking molecules 16A, 16B, 16C include a functional group at one end to attach to a functional group of the polymeric hydrogel 42, a functional group at the other end to attach to a functional group of the dark quencher 44, and a cleavage site 22. In the examples depicted in FIG. 1, an alkyne functional group is present at one end of the cleavable linking molecule and can attach to an azide functional group of the polymeric hydrogel 42. The emission quenching portion of the dark quencher 44 includes a functional group that can attach to the carbonyl of the cleavable linking molecules 16A, 16B, 16C. The cleavable linking molecule 16A includes a vicinal diol cleavage site 22, which can be cleaved via exposure to a sodium periodate. The cleavable linking molecule 16B includes an ester cleavage site 22', which can be cleaved via a base. The cleavable linking molecule 16C includes an O-azidomethyl cleavage site 22", which can be cleaved via a phosphine, such as tris(2-carboxyethyl)phosphine (TCEP) or tri(hydroxypropyl)phosphine (THP).

In other examples, the cleavable linking molecule includes a non-covalent binding pair. Examples of non-covalent binding pairs include a NiNTA (nickel-nitrilotriacetic acid) ligand and a histidine tag, or streptavidin or avidin and biotin, or a spytag and a spycatcher. As one specific example, streptavidin or avidin is attached to an end of the dark quencher 44 and biotin is attached to the polymeric hydrogel 42. As another specific example, biotin is attached to an end of the dark quencher 44 and streptavidin or avidin is attached to the polymeric hydrogel 42. In these specific examples, hot formamide may be used as a cleaving agent if/when it is desirable to remove the dark quencher 44. Other protein binding mechanisms aside from streptavidin, or avidin and biotin, may also be used.

When biotin is attached to the polymeric hydrogel 42, the biotin itself may be attached to the polymeric hydrogel 42 through a linker, such as biotoin-PEG4-alkyne or DBCO-S—S-PEG3-biotin (the latter of which includes a cleavable disulfide bond). When the biotin linker includes the disulfide bond, it can be removed when exposed to a reducing agent, such as TCEP (tris(2-carboxyethyl)phosphine) or DTT (dithiothreitol). These types of reducing reagents may be used in some sequencing operations, and thus this type of biotin linker may not be desirable when the dark quencher 44 is to be used for SNR reduction. Alternatively, the complete removal of the polymeric hydrogel 42 bound portion of the non-covalent binding pair (e.g., biotin) may be desirable when the dark quencher 44 is used as a security feature in a fluorescent sensor. As such, in these instances, the biotin linker including the disulfide bond may be desirable.

In some examples where the dark quencher 44 is used to reduce SNR, the length of the cleavable linking molecule is selected so that the dark quencher 44 is within signal quenching proximity of the surface of the polymeric hydrogel 42 where non-specifically bound molecules of interest may be located during optical detection of incorporated or otherwise sequestered molecules of interest. In one example, the length of the cleavable linking molecule ranges from about 0.25 nm to about 8 nm. In another example, the length of the cleavable linking molecule ranges from about 0.5 nm to about 4 nm.

In other examples where the dark quencher 44 is used as a security feature, the length of the cleavable linking molecule is selected so that the dark quencher 44 is within signal quenching proximity of a predetermined distance from the 3' end of the primers attached to the polymeric hydrogel 42, or from another capture substance attached to the polymeric hydrogel 42. This predetermined distance depends, in part, upon the length of the molecule of interest, because the dark quencher 44 is to suppress the molecule of interest’s emission during incorporation. In some instances, this distance may also depend upon the depth of a depression where the polymeric hydrogel 42 is located. In an example where a library fragment to be sequenced includes from 50 nucleotides (base pairs) to 550 nucleotides (base pairs), the cleavable linking molecule may have a length ranging from about 20 nm to about 500 nm.

In other examples, the polymeric hydrogel 42 has the dark quencher 44 incorporated into its backbone chain. In this example, structure (I) (or any variation thereof) would incorporate the dark quencher 44 as an additional monomeric unit. In these instances, the emission quenching portion of the dark quenchers 44 disclosed herein may be modified with a polymerizable group, such as an acrylamide or an acrylate. As examples, any of the phosphoramidite groups in the BHQ® examples set forth herein may be replaced with an acrylamide group, which can be copolymerized with the other monomers set forth herein. One specific example of a dark quencher 44 containing monomeric unit is:

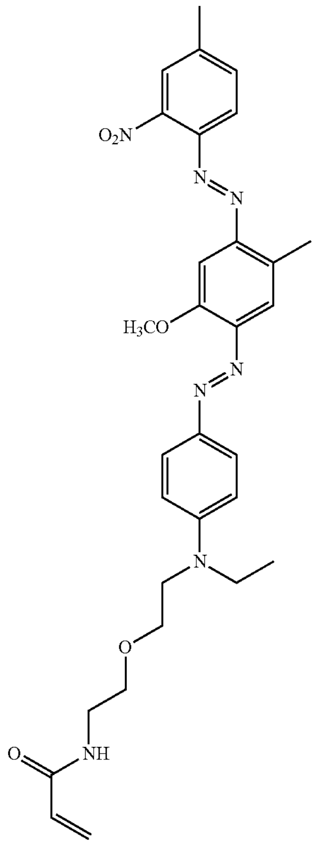 [SMILES: C=CC(=O)NCCOCCN(CC)c1ccc(/N=N/c2cc(C)c(/N=N/c3ccc(C)cc3[N+](=O)[O-])cc2OC)cc1]

In some of these examples, the dark quencher 44 is present in an amount ranging from about 0.25 mol % to about 50 mol % relative to a total number of moles in the polymeric hydrogel 42.

The incorporation of the dark quencher 44 into the polymeric hydrogel 42 backbone places the dark quencher 44 at the polymeric hydrogel surface, and thus within signal quenching proximity of the hydrogel surface where non-specifically bound molecules of interest may be located during optical detection of incorporated or otherwise sequestered molecules of interest.

In still other examples, the dark quencher 44 is covalently attached to the polymeric hydrogel 42 through a linking molecule. In these examples, the linking molecule capable of covalent attachment may be cleavable (examples of which are described herein with the cleavable linking molecule) or un-cleavable.

Figure 2:
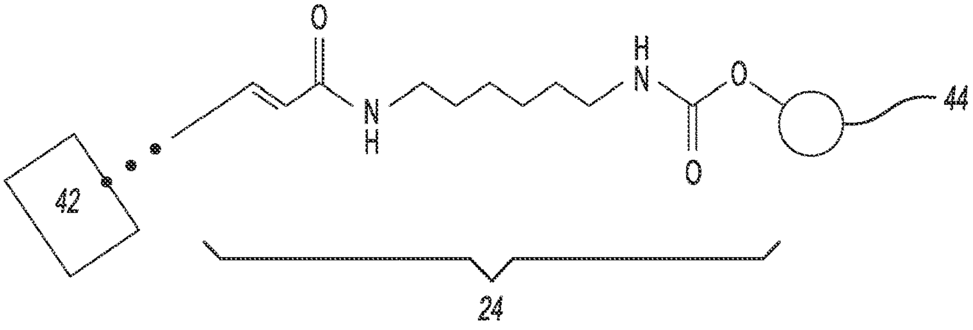
FIG. 2 depicts a schematic illustration of a chemical structure of an example of a non-cleavable linking molecule attaching a dark quencher to a polymeric hydrogel.

An example of an un-cleavable linking molecule is shown at reference numeral 24 of FIG. 2. In this example, the un-cleavable linking molecule 24 includes a functional group at one end to attach to a functional group of the polymeric hydrogel 42, and a functional group at the other end to attach to a functional group of the dark quencher 44. The un-cleavable linking molecule 24 does not include a cleavage site 22.

In some examples, the linking molecule is a non-oligonucleotide linker, and the linking molecule is present in an amount ranging from about 0.25 mol % to about 50 mol % relative to a total number of moles in the polymeric hydrogel 42. From about 0.5% to 100% of the attached linking molecules may have the dark quencher 44 attached thereto. Examples of non-oligonucleotide linkers may include a spacer group of formula $—((CH_2)_2O)_n—$, wherein n is an integer between 2 and 50, a carbon chain, a polyether, a peptide linker, a polyamide linker, bicycle[6.1.0]nonyne, etc. or the like. As one example, the emission quenching portion of the dark quenchers 44 disclosed herein may be modified with bicycle[6.1.0]nonyne, which can covalently attach to an azide of the polymeric hydrogel 42. One specific example of a bicycle[6.1.0]nonyne modified dark quencher 44 is:

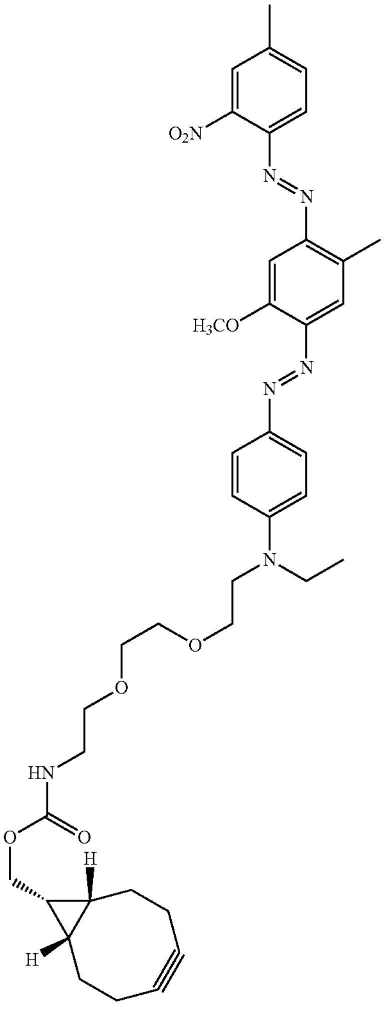 [SMILES: CCN(CCOCCOCCNC(=O)OC[C@@H]1[C@@H]2CCC#CCC[C@@H]21)c1ccc(/N=N/c2cc(C)c(/N=N/c3ccc(C)cc3[N+](=O)[O-])cc2OC)cc1]

In other of these examples, the linking molecule is an oligonucleotide linker, the polymeric hydrogel 42 includes a plurality of a functional group that is to attach to the oligonucleotide linker, and the oligonucleotide linker is present in an amount sufficient to occupy from about 0.5% to about 50% of the plurality of the functional group. In an example, the functional group of the polymeric hydrogel 42 that can attach the oligonucleotide linker may be an azide or an amine or any of the $R^A$ groups set forth herein for structure (I). Examples of suitable oligonucleotide linkers have 10 nucleotides or less. In examples where primers are to be attached to the polymeric hydrogel 42, it is to be understood that the oligonucleotide linkers do not have the same sequence as the primers or nucleic acid linker attached to the primers. An example of a nucleic acid linker is a polyT spacer, although other nucleotides can also be used. In one example, the spacer is a 6T to 10T spacer.

The length of the linking molecule is selected so that the dark quencher 44 is within signal quenching proximity of the surface of the polymeric hydrogel 42 where non-specifically bound molecules of interest may be located during optical detection of incorporated or otherwise sequestered molecules of interest. In one example, the length of the linking molecule ranges from about 0.25 nm to about 8 nm. In another example, the length of the linking molecule ranges from about 0.5 nm to about 4 nm.

In some examples described herein, the dark quencher 44 is attached to the polymeric hydrogel 42 through a hairpin oligonucleotide (i.e., HP oligo) or a DNA origami. One end of the hairpin oligonucleotide or DNA origami has a functional group to attach to the polymeric hydrogel 42 and the other end of the hairpin oligonucleotide or DNA origami has a functional group to attach to the dark quencher 44. Each of these attachment mechanisms may be used for SNR reduction or as a security feature.

When used for SNR reduction, the overlapping region of the hairpin oligonucleotide is selected to be short so that when the strand is fully extended (e.g., at the outset of a sequencing or other detection operation), the dark quencher 44 at the end of the hairpin oligonucleotide is within signal quenching proximity of the surface of the polymeric hydrogel 42. When used as a security feature, the overlapping region of the hairpin oligonucleotide is selected to be long so that when the strand is fully extended (e.g., at the outset of a sequencing or other detection operation), the dark quencher 44 at the end of the hairpin oligonucleotide is within signal quenching proximity of the molecule of interest as it is incorporated into a nascent strand or otherwise captured.

DNA origami structures are commercially available in lengths ranging from about 10 nm to about 100 nm. When used for SNR reduction, the length of the DNA origami structure is selected so that the dark quencher 44 is within signal quenching proximity of the surface of the polymeric hydrogel 42. When used as a security feature, the length of the DNA origami structure is selected so that the dark quencher 44 at the end of the DNA origami structure is within signal quenching proximity of the molecule of interest as it is incorporated into a nascent strand or otherwise captured.

Any example of the dark quencher 44 may be selected to exhibit absorption at one or more wavelengths ranging from about 400 nm to about 670 nm.

The hydrogel material for the polymeric hydrogel 42 may be formed using any suitable copolymerization process, such as nitroxide mediated polymerization (NMP), reversible addition-fragmentation chain-transfer (RAFT) polymerization, atom transfer radical polymerization (ATRP), etc. When the dark quencher 44 is incorporated into the polymeric hydrogel backbone, monomer(s) containing the dark quencher 44 may be used in the polymerization process to form the copolymer. When the dark quencher 44 is attached to the polymeric hydrogel 42 via a linker or binding pair, the dark quencher 44 may be grafted to the polymeric hydrogel 42 post-polymerization.

Flow Cells

One application in which the polymeric hydrogel 42 and the dark quencher 44 may be used is as part of flow cell surface chemistry.

One example of the flow cell described herein generally includes the substrate having a surface and the polymeric hydrogel 42 attached to at least a portion of the substrate surface, the polymeric hydrogel 42 including the dark quencher 44 and at least one primer set attached to the polymeric hydrogel 42.

Figures 3A, 3B, 3C, 3D:
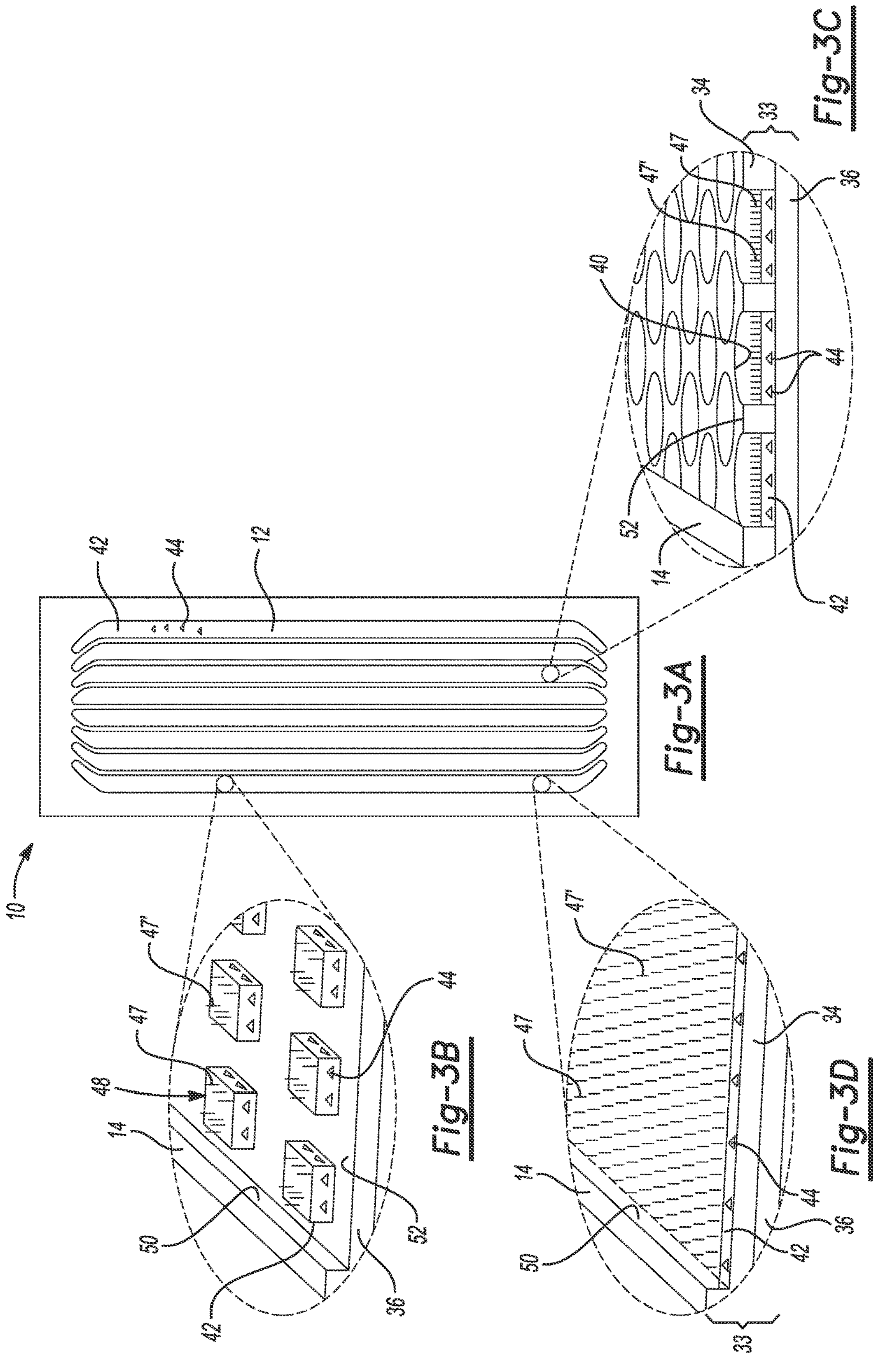
FIG. 3A is a top view of an example of a flow cell.
FIG. 3B through FIG. 3D are enlarged, and partially cutaway views of different examples of architectures in a flow channel of a flow cell.

One example of a flow cell 10 is shown in FIG. 3A from a top view. The flow cell 10 may include two patterned structures bonded together or one patterned structure bonded to a lid (lid not shown). Between the two patterned structures or the one patterned structure and the lid is a flow channel 12. The example flow cell 10 shown in FIG. 3A includes eight flow channels 12. While eight flow channels 12 are shown in FIG. 3A, it is to be understood that any number of flow channels 12 may be included in the flow cell 10 (e.g., a single flow channel 12, four flow channels 12, etc.). Each flow channel 12 may be isolated from each other flow channel 12 so that fluid introduced into a flow channel 12 does not flow into adjacent flow channel(s) 12. Some examples of the fluids introduced into the flow channel 12 may introduce reaction components (e.g., DNA sample(s), polymerases, sequencing primers, nucleotides, etc.), washing solutions, deblocking agents, etc.

Each flow channel 12 is in fluid communication with an inlet and an outlet (not shown). The inlet and outlet of each flow channel 12 may be positioned at opposed ends of the flow cell 10. The inlets and outlets of the respective flow channels 12 may alternatively be positioned anywhere along the length and width of the flow channel 12 that enables desirable fluid flow.

The inlet allows fluids to be introduced into the flow channel 12, and the outlet allows fluid to be extracted from the flow channel 12. Each of the inlets and outlets is fluidly connected to a fluidic control system (including, e.g., reservoirs, pumps, valves, waste containers, and the like) which controls fluid introduction and expulsion.

The flow channel 12 is at least partially defined by a patterned structure. The patterned structure may include a substrate, such as the single layer base support 36 (as shown in FIG. 3B), or the multi-layered structure 33 including a base support 36 and at least one other layer 34 on the base support 36 (as shown in FIG. 3C and FIG. 3D).

Examples of suitable single layer base supports 36 include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HfO_2$), carbon, metals, inorganic glasses, or the like.

Examples of the multi-layered structure 33 include the base support 36 and at least one other layer 34 on the base support. Some examples of the multi-layered structure 33 include glass or silicon as the base support 36, with a coating layer 34 of tantalum oxide (e.g., tantalum pentoxide or another tantalum oxide(s) ($TaO_x$)) or another ceramic oxide at the surface. Other examples of the multi-layered structure 33 include the base support 36 (e.g., glass, silicon, tantalum pentoxide, or any of the other base support materials) and a patterned resin as the other layer 34. It is to be understood that any material that can be selectively deposited, or deposited and patterned to form depressions 40 and interstitial regions 52 (see FIG. 3C) may be used for the patterned resin.

As one example of the patterned resin, an inorganic oxide may be selectively applied to the base support 36 via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example of the patterned resin, a polymeric resin may be applied to the base support 36 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, etc. Some examples of suitable resins include a polyhedral oligomeric silsesquioxane resin based resin, an epoxy resin not based on a polyhedral oligomeric silsesquioxane, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (commercially available as POSS® from Hybrid Plastics) refers to a chemical composition that is a hybrid intermediate (e.g., $RSiO_{1.5}$) between that of silica ($SiO_2$) and silicone ($R_2SiO$). An example of a polyhedral oligomeric silsesquioxane may be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups.

In an example, the single base support 36 (whether used singly or as part of the multi-layered structure 33) may be a circular sheet, a panel, a wafer, a die etc. having a diameter ranging from about 2 mm to about 300 mm, e.g., from about 200 mm to about 300 mm, or may be a rectangular sheet, panel, wafer, die etc. having its largest dimension up to about 10 feet (~3 meters). For example, a die may have a width ranging from about 0.1 mm to about 10 mm. While example dimensions have been provided, it is to be understood that a single base support with any suitable dimensions may be used.

In an example, the flow channel 12 has a substantially rectangular configuration (e.g., with curved ends, as shown in FIG. 3A). The length and width of the flow channel 12 may be selected so that a portion of the base support 36 or the multi-layer structure 33 of the flow cell 10 surrounds the flow channel 12 and is available for attachment to the lid (not shown) or another patterned structure.

The depth of the flow channel 12 can be as small as a monolayer thick when microcontact, aerosol, or inkjet printing is used to deposit a separate material (not shown) that defines the flow channel 12 walls. For other examples, the depth of the flow channel 12 can be about 1 μm, about 10 μm, about 50 μm, about 100 μm, or more. In an example, the depth may range from about 10 μm to about 100 μm. In another example, the depth may range from about 10 μm to about 30 μm. In still another example, the depth is about 5 μm or less. It is to be understood that the depth of the flow channel 12 may be greater than, less than or between the values specified above.

FIG. 3B, FIG. 3C, and FIG. 3D depict examples of architecture(s) within the flow channel 12.

The architecture shown in FIG. 3B is one example of a patterned structure. In this example, the polymeric hydrogel 42 (and in some instances, 42A, 42B as discussed further in reference to FIG. 4A through FIG. 4D) is applied to the substrate surface as a plurality of pads 48, wherein each of the plurality of pads 48 is isolated from each other of the plurality of pads 48 by interstitial regions 52. The pads 48 are positioned within a lane 50 defined in the single layer base support 36. While the substrate shown in FIG. 3B is the single layer base support 36, it is to be understood that the multi-layer structure 33 may be used (where the pads 48 would be formed in a lane 50 defined in the other layer 34).

Any example of the polymeric hydrogel 42 (including the dark quencher 44) may be used and may be formed via the techniques described herein. In the example shown in FIG. 3B, the polymeric hydrogel 42 is deposited to form isolated pads 48. The polymeric hydrogel 42 may be selectively applied using masked deposition techniques. Prior to generating the polymeric hydrogel pads 48, the surface of the single layer base support 36 may be selectively activated, and then a mixture (including the polymeric hydrogel 42 and the dark quencher 44) may be selectively applied thereto. In one example, a silane or silane derivative (e.g., norbornene silane) may be deposited on the surface of the single layer base support 36 using selective deposition processes, which may or may not utilize a mask. In another example, the single layer base support 36 may be selectively exposed to plasma ashing to generate surface-activating agent(s) (e.g., —OH groups) that can adhere to the polymeric hydrogel 42. The polymeric hydrogel 42 may then be coated using any suitable deposition technique, such as spray coating, spin coating, dunk coating, dip coating, etc. where the hydrogel 42 attaches to the activated portions alone.

The architecture shown in FIG. 3C is another example of a patterned structure. In these examples, the flow cell 10 includes a plurality of depressions 40 defined in the substrate surface, which are isolated from each other by interstitial regions 52. Each of the plurality of depressions 40 has the polymeric hydrogel 42 applied therein. The substrate of this patterned structure is the multi-layered structure 33 with depressions 40 defined in the layer 34. While the substrate shown in FIG. 3C is the multi-layer structure 33, it is to be understood that the single layer base support 36 may be used (where the depressions 40 would be formed in a lane 50 defined in the single layer base support 36).

The depressions 40 may be formed using any suitable patterning techniques, such as photolithography, nanoimprint lithography (NIL), stamping techniques, embossing techniques, molding techniques, microetching techniques, etc.

The depressions 40 provide a designated area for the polymeric hydrogel 42. Any example of the polymeric hydrogel 42 (including the dark quencher 44) may be used and may be formed via the techniques described herein.

To introduce the polymeric hydrogel 42 into the depressions 40, the mixture of the polymeric hydrogel 42 (which includes the dark quencher 44) may be generated and then applied to the multi-layered structure 33. In one example, the polymeric hydrogel 42 may be present in a mixture with water or with ethanol and water. The mixture may then be applied to the substrate surface using spin coating, or dipping or dip coating, or flow of the material under positive or negative pressure, or another suitable technique. These types of techniques blanketly deposit the polymeric hydrogel 42 in the depressions 40 and on the interstitial regions 52. Other selective deposition techniques (e.g., involving a mask, controlled printing techniques, etc.) may be used to specifically deposit the polymeric hydrogel 42 in the depressions 40 and not on the interstitial regions 52.

In some examples, the surface of the layer 34 (including the depressions 40) may be activated, and then the mixture (including the polymeric hydrogel 42) may be applied thereto. In one example, a silane or silane derivative (e.g., norbornene silane) may be deposited on the surface of the layer 34 using vapor deposition, spin coating, or other deposition methods. In another example, the layer 34 may be exposed to plasma ashing to generate surface-activating agent(s) (e.g., —OH groups) that can adhere to the polymeric hydrogel 42.

Depending upon the chemistry of the polymeric hydrogel 42, the applied mixture may be exposed to a curing process. In an example, curing may take place at a temperature ranging from room temperature (e.g., about 25° C.) to about 95° C. for a time ranging from about 1 millisecond to about several days.

Polishing may then be performed in order to remove the polymeric hydrogel 42 from the interstitial regions 52, while leaving the polymeric hydrogel 42 on the surface in the depressions 40 at least substantially intact. The polishing process may be performed with a chemical slurry (including, e.g., an abrasive, a buffer, a chelating agent, a surfactant, and/or a dispersant) which can remove the polymeric hydrogel 42 from the interstitial regions 52 without deleteriously affecting the underlying substrate at those regions 52. Alternatively, polishing may be performed with a solution that does not include the abrasive particles.

The chemical slurry may be used in a chemical mechanical polishing system (including (a) polishing head(s)/pad(s) or other polishing tool(s)) to polish the surface of the interstitial regions 52. The polishing head(s)/pad(s) or other polishing tool(s) is/are capable of polishing the polymeric hydrogel 42 that may be present over the interstitial regions 52 while leaving the polymeric hydrogel 42 in the depressions 40 at least substantially intact. As an example, the polishing head may be a Strasbaugh ViPRR II polishing head.

Cleaning and drying processes may be performed after polishing. The cleaning process may utilize a water bath and sonication. The water bath may be maintained at a relatively low temperature ranging from about 22° C. to about 30° C. The drying process may involve spin drying, or drying via another suitable technique.

Many different layouts of the plurality of pads 48 or depressions 40 and interstitial regions 52 may be envisaged, including regular, repeating, and non-regular patterns. In an example, the plurality of pads 48 and/or depressions 40 and interstitial regions 52 is/are disposed to create a hexagonal grid for close packing and improved density. Other layouts may include, for example, rectangular layouts, triangular layouts, and so forth. In some examples, the layout or pattern can be an x-y format in rows and columns. In some other examples, the layout or pattern can be a repeating arrangement of the plurality of pads 48 or depressions 40 and the interstitial regions 52. In still other examples, the layout or pattern can be a random arrangement of the plurality of pads 48 or depressions 40 and the interstitial regions 52.

The layout or pattern may be characterized with respect to the density (number) of the plurality of pads 48 or depressions 40 within a defined area. For example, the plurality of pads 48 or depressions 40 may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density can be between one of the lower values and one of the upper values selected from the ranges above, or that other densities (outside of the given ranges) may be used. As examples, a high density array may be characterized as having the plurality of pads 48 and/or depressions 40 separated by less than about 100 nm, a medium density array may be characterized as having the plurality of pads 48 and/or depressions 40 separated by about 400 nm to about 1 μm, and a low density array may be characterized as having the plurality of pads 48 and/or depressions 40 separated by greater than about 1 μm.

The layout or pattern of the plurality of pads 48 and/or depressions 40 may also or alternatively be characterized in terms of the average pitch, or the spacing from the center of one polymeric hydrogel pad 48 and/or depression 40 to the center of an adjacent polymeric hydrogel pad 48 and/or depression 40 (center-to-center spacing) or from the right edge of one of the plurality of pads 48 and/or depressions 40 to the left edge of an adjacent pad 48 and/or depression 40 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.15 μm, about 0.5 μm, about 1 μm, about 5 μm, about 10 μm, about 100 μm, or more or less. The average pitch for a particular pattern of can be between one of the lower values and one of the upper values selected from the ranges above. In an example, the depressions 40 have a pitch (center-to-center spacing) of about 1.5 μm. While example average pitch values have been provided, it is to be understood that other average pitch values may be used.

The size of each polymeric hydrogel pad 48 may be characterized by its top surface area, height, and/or diameter (when the pad 48 is circular) and/or length and width. In an example, the top surface area can range from about $1\times10^{-3}$ $\mu m^2$ to about 100 $\mu m^2$, e.g., about $1\times10^{-2}$ $\mu m^2$, about 0.1 $\mu m^2$, about 1 $\mu m^2$, at least about 10 $\mu m^2$, or more, or less. For still another example, the height can range from about 0.1 μm to about 100 μm, e.g., about 0.5 μm, about 1 μm, about 10 μm, or more, or less. For yet another example, the diameter or each of the length and width can range from about 0.1 μm to about 100 μm, e.g., about 0.5 μm, about 1 μm, about 10 μm, or more, or less.

The size of each depression 40 may be characterized by its volume, opening area, depth, and/or diameter (when the depression 40 is circular) and/or length and width. For example, the volume can range from about $1\times10^{-3}$ $\mu m^3$ to about 100 $\mu m^3$, e.g., about $1\times10^{-2}$ $\mu m^3$, about 0.1 $\mu m^3$, about 1 $\mu m^3$, about 10 $\mu m^3$, or more, or less. For another example, the opening area can range from about $1\times10^{-3}$ $\mu m^2$ to about 100 $\mu m^2$, e.g., about $1\times10^{-2}$ $\mu m^2$, about 0.1 $\mu m^2$, about 1 $\mu m^2$, at least about 10 $\mu m^2$, or more, or less. For still another example, the depth can range from about 0.1 μm to about 100 μm, e.g., about 0.5 μm, about 1 μm, about 10 μm, or more, or less. For another example, the depth can range from about 0.1 μm to about 100 μm, e.g., about 0.5 μm, about 1 μm, about 10 μm, or more, or less. For yet another example, the diameter or each of the length and width can range from about 0.1 μm to about 100 μm, e.g., about 0.5 μm, about 1 μm, about 10 μm, or more, or less.

The architectures in both FIG. 3B and FIG. 3C may include edge regions 14 that define interstitial like regions that extend the length of the flow channels 12 and separate one flow channel 12 from an adjacent flow channel 12. The edge regions 14 provide bonding regions where two non-patterned structures can be attached to one another or where one non-patterned structure can be attached to a lid (not shown).

The architectures in both FIG. 3B and FIG. 3C include a primer set, which includes two primers 47, 47'. The primers 47, 47' are attached to the polymeric hydrogel 42.

In this example, the primers 47, 47' are two different primers that are used in sequential paired end sequencing. As examples, the primers 47, 47' may include P5 and P7 primers, P15 and P7 primers, or any combination of the PA primers, the PB primers, the PC primers, and the PD primers set forth herein. As examples, the primers 47, 47' may include any two PA, PB, PC, and PD primers, or any combination of one PA primer and one PB, PC, or PD primer, or any combination of one PB primer and one PC or PD primer, or any combination of one PC primer and one PD primer.

Examples of P5 and P7 primers are used on the surface of commercial flow cells sold by Illumina Inc. for sequencing, for example, on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms. The P5 primer is:

```
P5: 5' → 3'
                                (SEQ. ID. NO. 1)
AATGATACGGCGACCACCGAGAUCTACAC
```

The P7 primer may be any of the following:

```
P7#1: 5' → 3'
                                (SEQ. ID. NO. 2)
CAAGCAGAAGACGGCATACGAnAT

P7 #2: 5' → 3'
                                (SEQ. ID. NO. 3)
CAAGCAGAAGACGGCATACnAGAT
```

where "n" is 8-oxoguanine in each of the sequences.

The P15 primer is:

```
P15: 5' → 3'
                                (SEQ. ID. NO. 4)
AATGATACGGCGACCACCGAGAnCTACAC
```

where "n" is allyl-T.

The other primers (PA-PD) mentioned above include:

```
PA 5' → 3'
                                (SEQ. ID. NO. 5)
GCTGGCACGTCCGAACGCTTCGTTAATCCGTTGAG

PB 5' → 3'
                                (SEQ. ID. NO. 6)
CGTCGTCTGCCATGGCGCTTCGGTGGATATGAACT
```

-continued

```
PC 5' → 3'
                                (SEQ. ID. NO. 7)
ACGGCCGCTAATATCAACGCGTCGAATCCGCAACT

PD 5' → 3'
                                (SEQ. ID. NO. 8)
GCCGCGTTACGTTAGCCGGACTATTCGATGCAGC
```

While not shown in the example sequences for PA-PD, it is to be understood that any of these primers may include a cleavage site, such as uracil, 8-oxoguanine, allyl-T (or another allyl-nucleotide), etc. at any point in the strand.

Each of the primers disclosed herein may also include a polyT sequence at the 5' end of the primer sequence. In some examples, the polyT region includes from 2 T bases to 20 T bases. As specific examples, the polyT region may include 3, 4, 5, 6, 7, or 10 T bases.

Figure 4A:
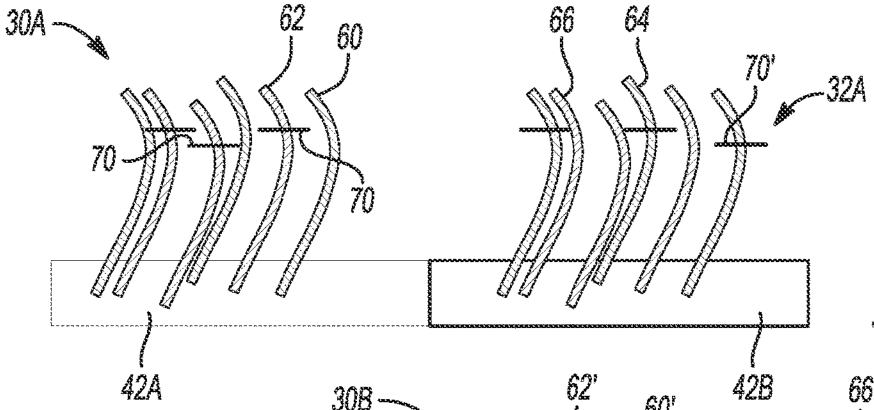
FIG. 4A through FIG. 4D are schematic views of different examples of primer sets that are used in some examples of flow cells disclosed herein.
Figure 4B:
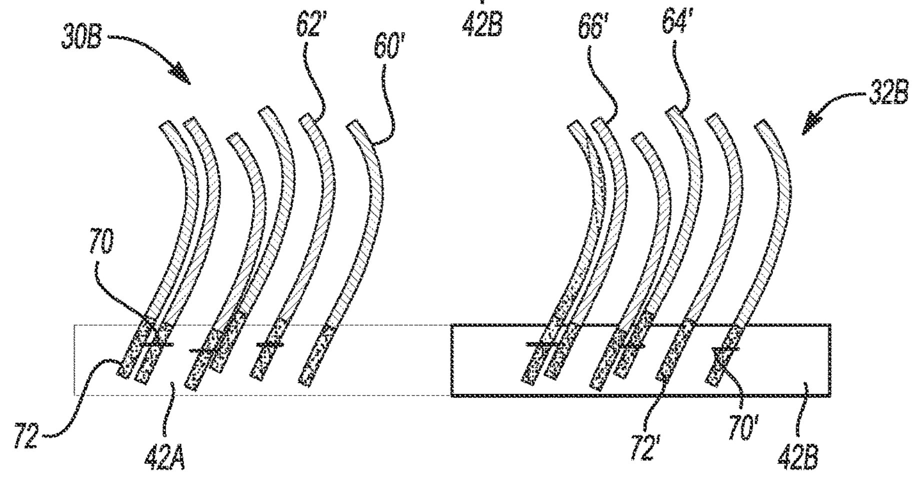
Figure 4C:
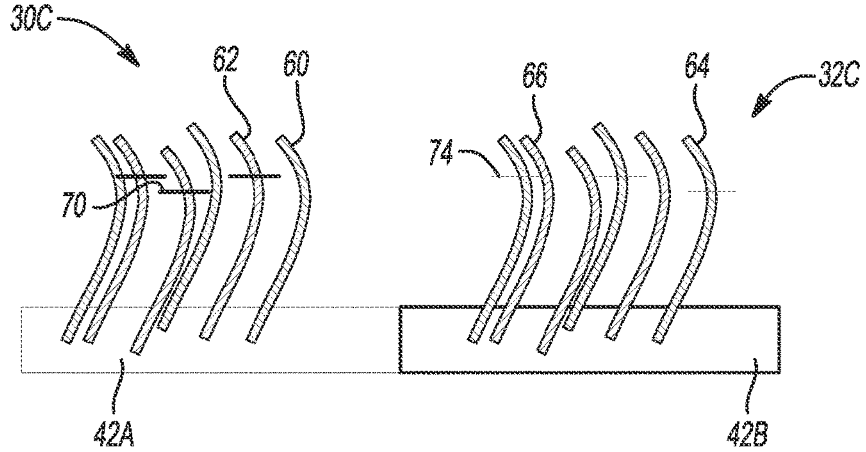
Figure 4D:
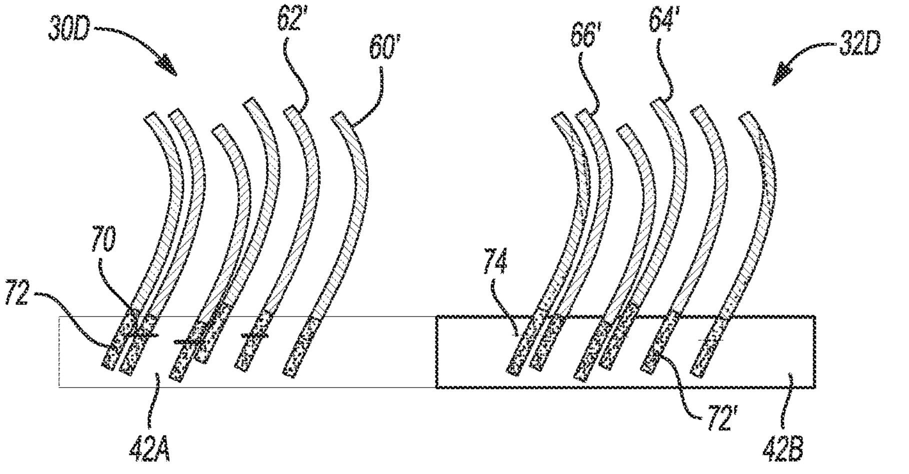

The 5' end of each primer may also include a linker (e.g., 72, 72') described in reference to FIG. 4B and FIG. 4D). Any linker 72, 72' that includes a terminal alkyne group or another suitable terminal functional group that can attach to the surface functional groups of the polymeric hydrogel 42 may be used. In one example, the primers are terminated with hexynyl.

In some examples, the primers 47, 47' may be pre-grafted to the polymeric hydrogel 42. In these examples, additional primer grafting is not performed. In other examples, the primers 47, 47' are not pre-grafted to the polymeric hydrogel 42. In these examples, the primers 47, 47' may be grafted after the polymeric hydrogel 42 is applied to the depressions 40.

When grafting is performed after the polymeric hydrogel 42 is applied, grafting may be accomplished using any suitable grafting techniques. As examples, grafting may be accomplished by flow through deposition (e.g., using a temporarily bound lid), dunk coating, spray coating, puddle dispensing, or by another suitable method. Each of these example techniques may utilize a primer solution or mixture, which may include the primers 47, 47', water, a buffer, and a catalyst. With any of the grafting methods, the primers 47, 47' attach to the reactive groups of the polymeric hydrogel 42 and have no affinity for the interstitial regions 52.

The architecture shown in FIG. 3D is a non-patterned structure. While the substrate shown in FIG. 3D is the multi-layer structure 33 (including the base support 36 and the other layer 34), it is to be understood that the substrate of the non-patterned structure may be either the single layer base support 36 or the multi-layer structure 33. In this example, a lane 50 is defined in the surface of the single layer base support 36 or in the surface of the multi-layer structure 33 surrounded by edge regions 14. The lane 50 may be formed using any suitable patterning techniques, such as photolithography, nanoimprint lithography (NIL), stamping techniques, embossing techniques, molding techniques, microetching techniques, etc.

The lane 50 provides a designated area for the polymeric hydrogel 42. The edge regions 14 provide bonding regions where two non-patterned structures can be attached to one another or where one non-patterned structure can be attached to a lid. As such, in this example, the surface of the flow cell is non-patterned, and the polymeric hydrogel 42 is positioned within the lane 50 of the non-patterned surface.

The attachment of the polymeric hydrogel 42 to the underlying single layer base support 36 or multi-layer structure 33 may be through covalent bonding. In some instances, the single layer base support 36 or multi-layer structure 33 may first be activated, e.g., through silanization or plasma ashing. Covalent linking is helpful for maintaining the primers 47, 47' in the desired regions throughout the lifetime of the flow cell 10 during a variety of uses.

It is to be understood that in these examples, the polymeric hydrogel 42 includes the dark quencher 44. Any example of the polymeric hydrogel 42 can be used in the non-patterned structure. The polymeric hydrogel 42 can be applied to the lane 50 as described in reference to FIG. 3C. If deposition and polishing techniques are used, the polishing would remove the polymeric hydrogel 42 from the edge region 14.

In these examples, the polymeric hydrogel 42 includes the primers 47, 47' attached thereto. In some examples, the primers 47, 47' may be pre-grafted to the polymeric hydrogel 42. In these examples, additional primer grafting is not performed. In other examples, the primers 47, 47' are not pre-grafted to the polymeric hydrogel 42. In these examples, the primers 47, 47' may be grafted after the polymeric hydrogel 42 is applied to the lane 50. Grafting may be performed using any suitable techniques described herein.

In any of the architectures shown in FIG. 3B through FIG. 3D, the polymeric hydrogel 42 may be configured to attach two different primer sets, examples of which are shown and described in reference to FIG. 4A through FIG. 4D. To attach two different primer sets, the polymeric hydrogel 42 may be divided into two different regions 42A, 42B as shown in FIG. 4A through FIG. 4D. In one example, the polymeric hydrogel 42 is chemically the same throughout the regions 42A, 42B, and suitable techniques may be used to immobilize the respective primer sets to the respective regions 42A, 42B. Examples of suitable techniques may include the use of a photoresist to pattern one region 42A and then the other region 42B, other masking techniques, etc. In another example, the regions 42A, 42B of the polymeric hydrogel 42 are chemically different (e.g., include different functional groups for respective primer set attachment), and any of the techniques disclosed herein may be used to immobilize the respective primer sets the respective polymeric hydrogel regions 42A, 42B. In other examples disclosed herein, respective samples of the polymeric hydrogel 42 may have the respective primer sets pre-grafted thereto, and thus the immobilization chemistries of the regions 42A, 42B of the polymeric hydrogel 42 may be the same or different.

Each of the two different primer sets 30A, 32A or 30B, 32B or 30C, 32C or 30D, 32D shown and described in reference to FIG. 4A through FIG. 4D are related in that one set includes an un-cleavable first primer and a cleavable second primer, and the other set includes a cleavable first primer and an un-cleavable second primer. These primer sets 30A, 32A or 30B, 32B or 30C, 32C or 30D, 32D allow a single template strand (i.e., library fragment) to be amplified and clustered across both primer sets 30A, 32A or 30B, 32B or 30C, 32C or 30D, 32D and also enable the generation of forward and reverse strands on adjacent polymeric hydrogel regions 42A, 42B due to the cleavage groups being present on the opposite primers of the sets 30A, 32A or 30B, 32B or 30C, 32C or 30D, 32D. Examples of these primer sets 30A, 32A or 30B, 32B or 30C, 32C or 30D, 32D will now be discussed in reference to FIG. 4A, FIG. 4B, FIG. 4C, and FIG. 4D.

FIG. 4A through FIG. 4D depict different configurations of the primer sets 30A, 32A or 30B, 32B or 30C, 32C or 30D, 32D, which may be attached to the polymeric hydrogel 42.

Each of the first primer sets 30A, 30B, 30C, and 30D includes an un-cleavable first primer 60 or 60' and a cleavable second primer 62 or 62'; and each of the second primer sets 32A, 32B, 32C, and 32D includes a cleavable first primer 64 or 64' and an un-cleavable second primer 66 or 66'.

The un-cleavable first primer 60 or 60' and the cleavable second primer 62 or 62' are oligonucleotide pairs, e.g., where the un-cleavable first primer 60 or 60' is a forward amplification primer and the cleavable second primer 62 or 62' is a reverse amplification primer or where the cleavable second primer 62 or 62' is the forward amplification primer and the un-cleavable first primer 60 or 60' is the reverse amplification primer. In each example of the first primer set 30A, 30B, 30C, and 30D the cleavable second primer 62 or 62' includes a cleavage site 70 while the un-cleavable first primer 60 or 60' does not include a cleavage site 70.

The cleavable first primer 64 or 64' and the un-cleavable second primer 66 or 66' are also oligonucleotide pairs, e.g., where the cleavable first primer 64 or 64' is a forward amplification primer and the un-cleavable second primer 66 or 66' is a reverse amplification primer or where the un-cleavable second primer 66 or 66' is the forward amplification primer and the cleavable first primer 64 or 64' is the reverse amplification primer. In each example of the second primer set 32A, 32B, 32C, and 32D, the cleavable first primer 64 or 64' includes a cleavage site 70', while the un-cleavable second primer 66 or 66' does not include a cleavage site 70'.

It is to be understood that the un-cleavable first primer 60 or 60' of the first primer set 30A, 30B, 30C, and 30D and the cleavable first primer 64 or 64' of the second primer set 32A, 32B, 32C, and 32D have the same nucleotide sequence (e.g., both are forward amplification primers), except that the cleavable first primer 64 or 64' includes the cleavage site 70' integrated into the nucleotide sequence or into a linker 72' attached to the nucleotide sequence. Similarly, the cleavable second primer 62 or 62' of the first primer set 30A, 30B, 30C, and 30D and the un-cleavable second primer 66 or 66' of the second primer set 32A, 32B, 32C, and 32D have the same nucleotide sequence (e.g., both are reverse amplification primers), except that the cleavable second primer 62 or 62' includes the cleavage site 70 integrated into the nucleotide sequence or into a linker 72 attached to the nucleotide sequence.

It is to be understood that when the first primers 60 and 64 or 60' and 64' are forward amplification primers, the second primers 62 and 66 or 62' and 66' are reverse primers, and vice versa.

The un-cleavable primers 60, 66 or 60', 66' may be any primers with a universal sequence for capture and/or amplification purposes, such as the P5 and P7 primers or any combination of the PA, PD, PC, PD primers (e.g., PA and PB or PA and PD, etc.). In some examples, the P5 and P7 primers are un-cleavable primers 60, 66 or 60', 66' because they do not include a cleavage site 70, 70' (e.g., "U" and "n" are respectively removed from the sequences shown in SEQ. ID. NOS. 1 and 2). It is to be understood that any suitable universal sequence can be used as the un-cleavable primers 60, 66 or 60', 66'.

Examples of cleavable primers 62, 64 or 62', 64' include the P5 and P7 primers or other universal sequence primers (e.g., the PA, PB, PC, PD primers) with the respective cleavage sites 70, 70' incorporated into the respective nucleic acid sequences (e.g., FIG. 4A and FIG. 4C), or into a linker 72, 72' that attaches the cleavable primers 62, 64 or 62', 64' to the respective polymeric hydrogel regions 42A, 42B (FIG. 4B and FIG. 4D). Examples of suitable cleavage sites 70, 70' include enzymatically cleavable nucleobases or chemically cleavable nucleobases, modified nucleobases, or linkers (e.g., between nucleobases), as described herein.

Each primer set 30A and 32A or 30B and 32B or 30C and 32C or 30D and 32D is attached to a respective region 42A, 42B of the polymeric hydrogel 42. As described herein, the polymeric hydrogel 42 may include different functional groups within the different regions 42A, 42B that can selectively react with the respective primers 60, 62 or 60', 62' or 64, 66 or 64', 66', or may include the same functional groups and the respective primers 60, 62 or 60', 62' or 64, 66 or 64', 66' may be sequentially attached via suitable methods.

While not shown in FIG. 4A through FIG. 4D, it is to be understood that one or both of the primer sets 30A, 30B, 30C, 30D or 32A, 32B, 32C or 32D may also include a PX primer for capturing a library template seeding molecule. As one example, PX may be included with the primer set 30A, 30B, 30C, 30D, but not with primer set 32A, 32B, 32C or 32D. As another example, PX may be included with the primer set 30A, 30B, 30C, 30D and with the primer set 32A, 32B, 32C or 32D. When the lane 50 is used, it may be desirable to space the PX primers along the length of the lane 50 near the interface of regions 42A, 42B. The density of the PX motifs should be relatively low (e.g., 1 PX primer in 1 depression 40) in order to minimize polyclonality within each pad 48, depression 40, or along the length of the region(s) 42A, 42B of the polymeric hydrogel 42 within the lane 50.

The PX capture primers may be:

```
PX 5' → 3'
                          (SEQ. ID. NO. 9)
AGGAGGAGGAGGAGGAGGAGGAGG

cPX (PX')5' → 3'
                          (SEQ. ID. NO. 10)
CCTCCTCCTCCTCCTCCTCCTCCT
```

FIG. 4A through FIG. 4D depict different configurations of the primer sets 30A, 32A, 30B, 32B, 30C, 32C, and 30D, 32D attached to regions 42A, 42B of the polymeric hydrogel 42. More specifically, FIG. 4A through FIG. 4D depict different configurations of the primers 60, 62 or 60', 62' and 64, 66 or 64', 66' that may be used.

In the example shown in FIG. 4A, the primers 60, 62 and 64, 66 of the primer sets 30A and 32A are directly attached to regions 42A, 42B, for example, without a linker 72, 72'. The region 42, A of the polymeric hydrogel 42 has surface functional groups that can immobilize the terminal groups at the 5' end of the primers 60, 62. Similarly, the region 42, B of polymeric hydrogel 42 has surface functional groups that can immobilize the terminal groups at the 5' end of the primers 64, 66. The immobilization chemistry between region 42, A and the primers 60, 62 and the immobilization chemistry between region 42, B and the primers 64, 66 may be different so that the primers 60, 62 or 64, 66 selectively attach to the desirable region 42A, 42B of the polymeric hydrogel 42. Alternatively, the primers 60, 62 or 64, 66 may be pre-grafted or sequentially applied via some of the methods disclosed herein.

Also, in the example shown in FIG. 4A, the cleavage site 70, 70' of each of the cleavable primers 62, 64 is incorporated into the sequence of the primer. In this example, the same type of cleavage site 70, 70' is used in the cleavable primers 62, 64 of the respective primer sets 30A, 32A. As an example, the cleavage sites 70, 70' are uracil bases, and the cleavable primers 62, 64 are P5U and P7U. The uracil bases or other cleavage sites may also be incorporated into any of the PA, PB, PC, and PD primers to generate the cleavable primers 62, 64. In this example, the un-cleavable primer 60 of the oligonucleotide pair 60, 62 may be P7, and the un-cleavable primer 66 of the oligonucleotide pair 64, 66 may be P5. Thus, in this example, the first primer set 30A includes P7, P5U and the second primer set 32A includes P5, P7U. The primer sets 30A, 32A have opposite linearization chemistries, which, after amplification, cluster generation, and linearization, allows forward template strands to be formed on one region 42, B and reverse strands to be formed on the other region 42, A.

In the example shown in FIG. 4B, the primers 60', 62' and 64', 66' of the primer sets 30B and 32B are attached to the regions 42A, 42B of the polymeric hydrogel 42, for example, through linkers 72, 72'. The regions 42A, 42B include respective functional groups, and the terminal ends of the respective linkers 72, 72' are capable of covalently attaching to the respective functional groups. As such, the region 42A may have surface functional groups that can immobilize the linker 72 at the 5' end of the primers 60', 62'. Similarly, region 42B may have surface functional groups that can immobilize the linker 72' at the 5' end of the primers 64', 66'. The immobilization chemistry for the region 42A and the linkers 72 and the immobilization chemistry for the region 42B and the linkers 72' may be different so that the primers 60', 62' or 64', 66' selectively attach to the desirable regions 42A, 42B of the polymeric hydrogel 42. Alternatively, the primers 60', 62' or 64', 66' may be pre-grafted or sequentially applied via some of the methods disclosed herein.

Examples of suitable linkers 72, 72' may include nucleic acid linkers (e.g., 10 nucleotides or less) or non-nucleic acid linkers, such as a polyethylene glycol chain, an alkyl group or a carbon chain, an aliphatic linker with vicinal diols, a peptide linker, etc. An example of a nucleic acid linker is a polyT spacer, although other nucleotides can also be used. In one example, the spacer is a 6T to 10T spacer. The following are some examples of nucleotides including non-nucleic acid linkers with terminal alkyne groups (where B is the nucleobase and "oligo" is the primer):

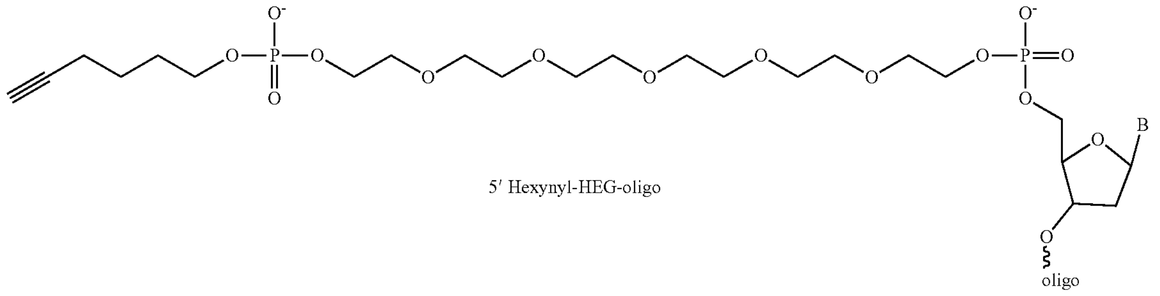

5' Hexynyl-HEG-oligo

-continued

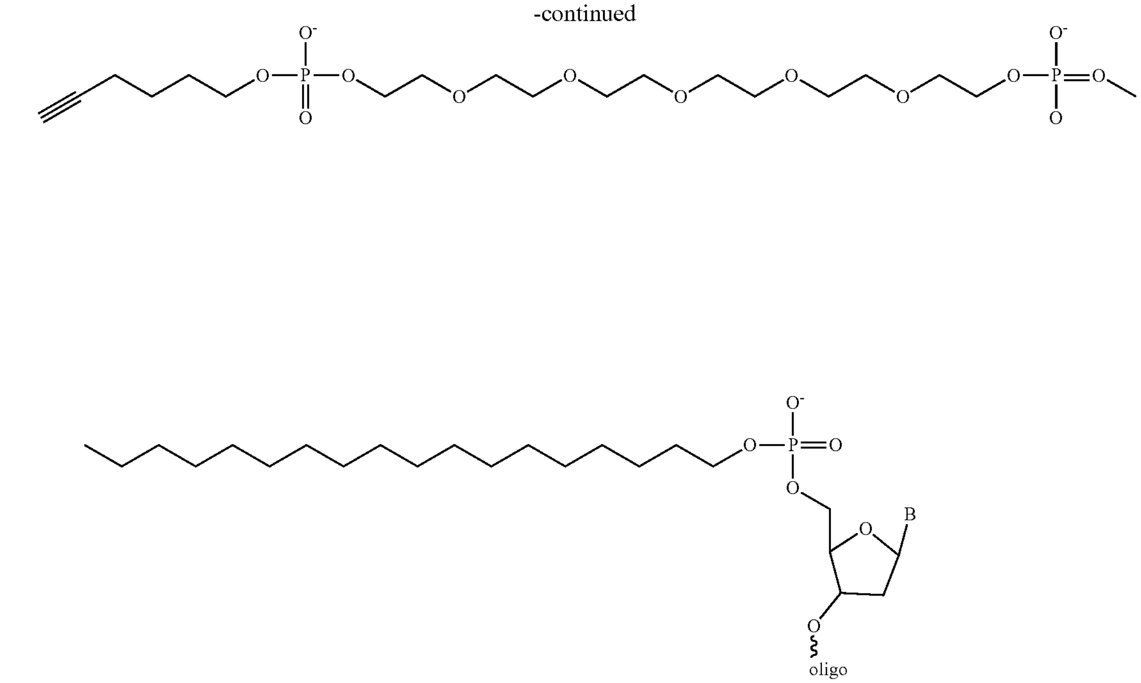

5′ Hexynyl-HEG-HEG-oligo

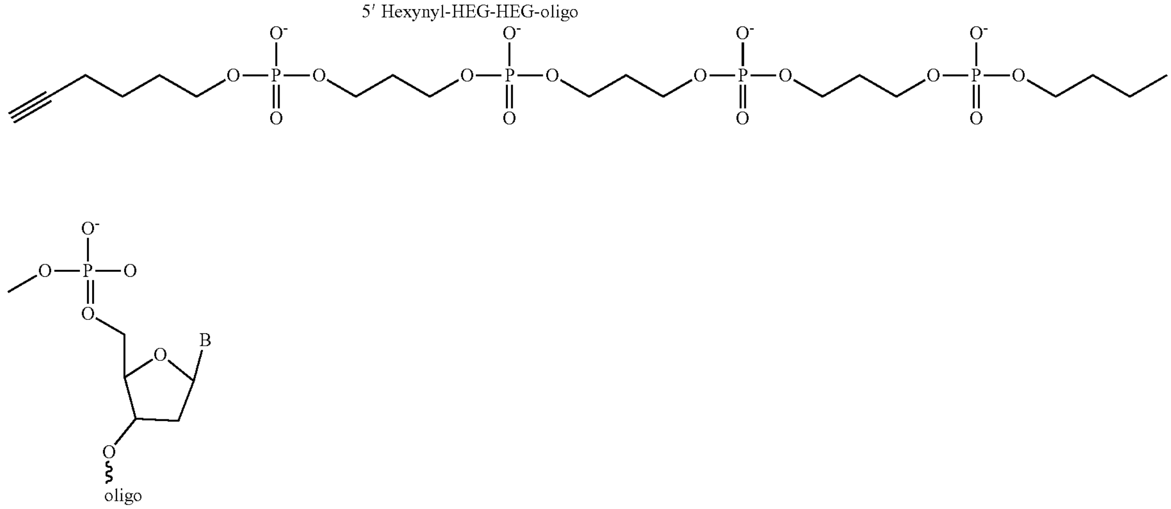

5′ Hexynyl-C3 spacer-C3 spacer-C3 spacer-C3 spacer-oligo

In the example shown in FIG. 4B, the primers 60', 64' have the same sequence (e.g., P5) and the same or different linker 72, 72'. The primer 60' is un-cleavable, whereas the primer 64' includes the cleavage site 70' incorporated into the linker 72'. Also in this example, the primers 62', 66' have the same sequence (e.g., P7) and the same or different linker 72, 72'. The primer 66' in un-cleavable, and the primer 62' includes the cleavage site 70 incorporated into the linker 72. The same type of cleavage site 70, 70' is used in the linker 72, 72' of each of the cleavable primers 62', 64'. As an example, the cleavage sites 70, 70' may be uracil bases that are incorporated into nucleic acid linkers 72, 72'. The primer sets 30B, 32B have opposite linearization chemistries, which, after amplification, cluster generation, and linearization, allows forward template strands to be formed on one region 42A and reverse strands to be formed on the other region 42B.

The example shown in FIG. 4C is similar to the example shown in FIG. 4A, except that different types of cleavage sites 70, 74 are used in the cleavable primers 62, 64 of the respective primer sets 30C, 32C. As examples, two different enzymatic cleavage sites may be used, two different chemical cleavage sites may be used, or one enzymatic cleavage site and one chemical cleavage site may be used. Examples of different cleavage sites 70, 74 that may be used in the respective cleavable primers 62, 64 include any combination of the following: vicinal diol, uracil, allyl ether, disulfide, restriction enzyme site, and 8-oxoguanine.

The example shown in FIG. 4D is similar to the example shown in FIG. 4B, except that different types of cleavage sites 70, 74 are used in the linkers 72, 72' attached to the cleavable primers 62', 64' of the respective primer sets 30D, 32D. Examples of different cleavage sites 70, 74 that may be used in the respective linkers 72, 72' attached to the cleavable primers 62', 64' include any combination of the following: vicinal diol, uracil, allyl ether, disulfide, restriction enzyme site, and 8-oxoguanine.

In any of the examples using the primers 47, 47' or the primer sets 30A, 32A, 30B, 32B, 30C, 32C, and 30D, 32D, the attachment of the primers 47, 47' or 60, 62 and 64, 66 or 60', 62' and 64', 66' to the polymeric hydrogel 42 leaves a template-specific portion of the primers 47, 47' or 60, 62 and 64, 66 or 60', 62' and 64', 66' free to anneal to its cognate template and the 3' hydroxyl group free for primer extension.

In each of the examples of the flow cell 10 disclosed herein, the polymeric hydrogel 42 including the dark quencher 44 and at least one primer set (e.g., primers 47, 47' or the primer sets 30A, 32A, 30B, 32B, 30C, 32C, and 30D, 32D) make up the surface chemistry of the patterned or non-patterned structure, and thus one surface of the flow cell 10. Thus, in some examples, the flow cell surface chemistry consists of the polymeric hydrogel 42 including the dark quencher 44 and at least one primer set (e.g., primers 47, 47' or the primer sets 30A, 32A, 30B, 32B, 30C, 32C, and 30D, 32D) attached to the polymeric hydrogel 42. Any example of the polymeric hydrogel 42, the dark quencher 44, and the at least one primer set (e.g., primers 47, 47' or the primer sets 30A, 32A, 30B, 32B, 30C, 32C, and 30D, 32D) disclosed herein may make up the surface chemistry.

Other Fluorescent Sensors

The polymeric hydrogel 42 and dark quencher 44 may be used is as part of surface chemistry in other types of fluorescent sensors.

One example of this other type of fluorescent sensor is a PCR sensor. In a PCR sensor, the polymeric hydrogel 42 and the dark quencher 44 make up at least a portion of the substrate surface, and the primers used in PCR would be attached thereto. In these examples, the PCR primers act as a capture substance for the DNA template strand to be amplified.

Another example of this other type of fluorescent sensor is an analyte-detection sensor. In an analyte-detection sensor, the polymeric hydrogel 42 and the dark quencher 44 make up at least a portion of the substrate surface, and the capture substance(s) used in the analyte-detection sensor would be attached thereto. In these examples, the capture substance may be a receptor for the analyte and the analyte may be a fluorophore or have a fluorophore attached thereto. The capture of the analyte (e.g., a protein) may be associated with emission quenching.

In still another example, the dark quencher 44 is attached to the polymeric hydrogel 42 or to the primer 47, 47'. This example of the polymeric hydrogel 42 also has a receptor or ligand attached thereto via additional primers or other tethers (e.g., polymeric linkers, etc.). The receptor or ligand is capable of capturing a target protein. In some instances, the target protein may also have a nucleic acid sequence attached thereto that includes an identifying region (e.g., a barcode region) that is to be amplified and sequenced for protein identification. In other instances, a ligand that includes the identifying region (that is to be amplified and sequenced) could be introduced to the flow cell and bound to the target protein. In either of these instances, the presence of the dark quencher 44 quenches emission. As such, a reagent may be introduced that removes the dark quencher. The reagent may be introduced prior to amplification of the identifying region, as part of the amplification reagents, or after amplification is performed. Thus, signal transduction from the proteins captured on the polymeric hydrogel 42 is in the form of signal recovery, as the dark quenchers 44 are removed prior to sequencing.

Method for Improving Signal-to-Noise Ratio

Figure 5:
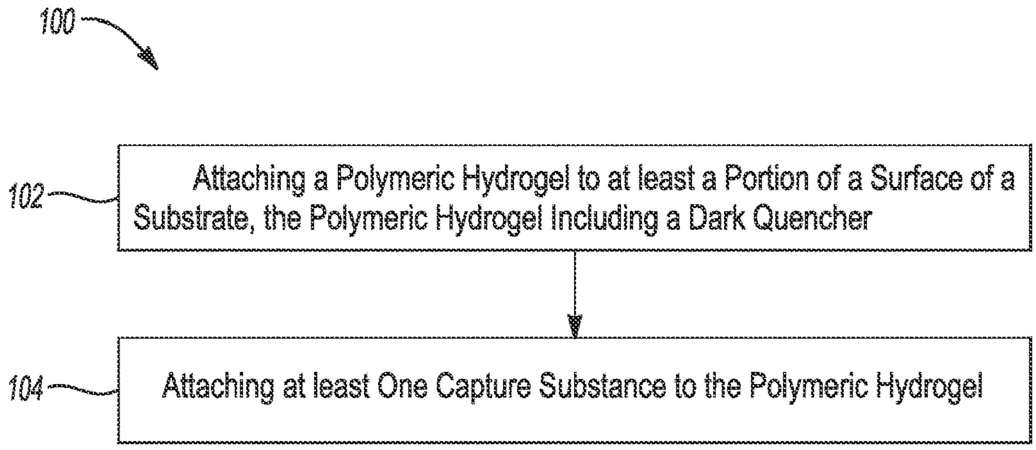
FIG. 5 is a flow diagram that illustrates an example of a method of improving a signal-to-noise ratio in a flow cell.

A method of improving a signal-to-noise ratio in a sensor that detects fluorescence is also disclosed herein. An example of the method 100 is shown in FIG. 5. An example of the method 100 comprises attaching a polymeric hydrogel 42 to at least a portion of a surface of a substrate, the polymeric hydrogel 42 including a dark quencher 44 (shown in reference numeral 102) and attaching at least one capture substance to the polymeric hydrogel 42 (shown in reference numeral 104).

Any of the flow cells 10 and other fluorescent sensors disclosed herein may be prepared using the method 100. When the flow cells and other fluorescent sensors are utilized in a sensing operation, the signal-to-noise ratio (SNR) is reduced due to the dark quencher 44 quenching the signals of non-specifically bound fully functionalized nucleotides.

Figure 6:
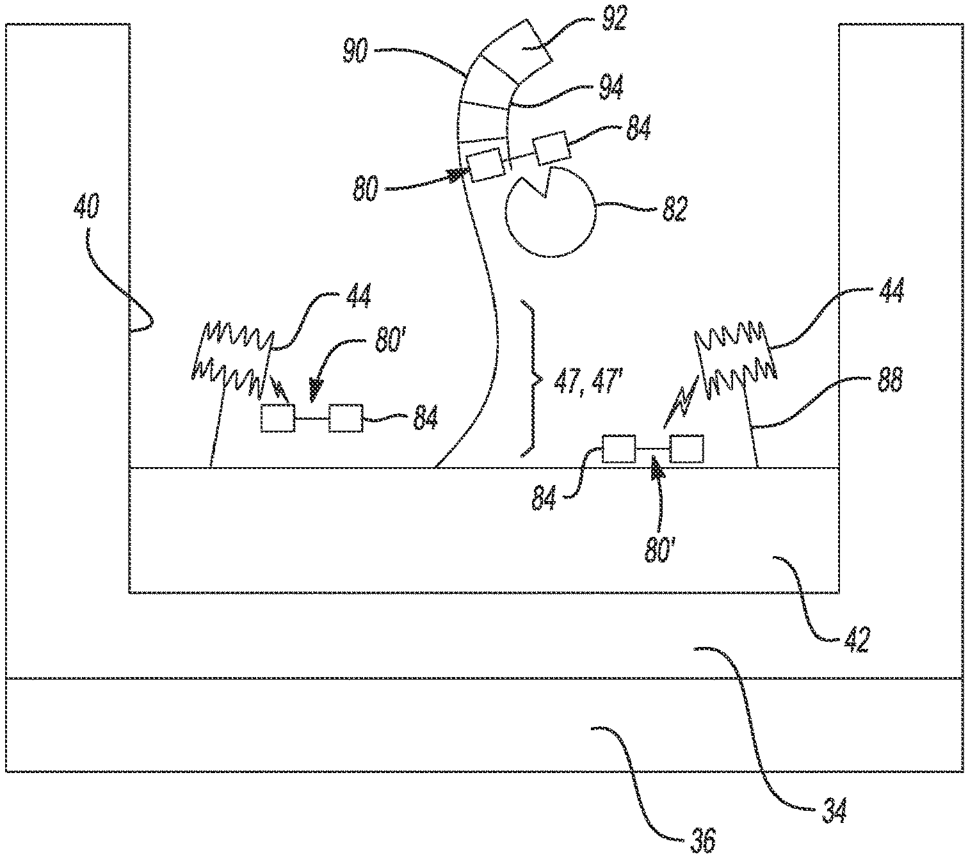
FIG. 6 is a schematic view that illustrates the effect(s) of a dark quencher on a non-specifically bound fluorophore.

Referring now to FIG. 6, one example of a sequencing-by-synthesis sensing operation utilizing one example of the flow cell 10 is schematically depicted. While the flow cell 10 depicted in FIG. 6 includes the multi-layer structure 33 (including the base support 36 and the other layer 34), it is to be understood that the single layer base support 36 may also be used. In this example, a single depression 40 of the flow cell 10 is depicted with the polymeric hydrogel 42 applied within the depression 40. Also in this example, the dark quencher 44 is attached to the polymeric hydrogel 42 via any example of linking molecules described herein, which are collectively shown at reference numeral 88. Alternatively, the dark quencher 44 could be incorporated into the backbone of the polymeric hydrogel 42. The primer(s) 47, 47' are also attached to the polymeric hydrogel 42.

During sequencing, a template strand 90 that is to be sequenced may be formed in the depression 40 using amplification primers 47, 47' immobilized on the polymeric hydrogel 42. At the outset of template strand formation, library fragments/templates may be prepared from any nucleic acid sample (e.g., a DNA sample or an RNA sample). The DNA nucleic acid sample may be fragmented into single-stranded, similarly sized (e.g., <1000 bp) DNA fragments. The RNA nucleic acid sample may be used to synthesize complementary DNA (cDNA), and the cDNA may be fragmented into single-stranded, similarly sized (e.g., <1000 bp) cDNA fragments. During preparation, adapters may be added to the ends of any of the fragments. Through reduced cycle amplification, different motifs may be introduced in the adapters, such as sequencing primer binding sites, indices, and regions that are complementary to the amplification primers 47, 47'. In some examples, the fragments from a single nucleic acid sample have the same adapters added thereto. The final library templates include the DNA or cDNA fragment and adapters at both ends. The DNA or cDNA fragment represents the portion of the final library template that is to be sequenced.

A plurality of library templates may be introduced to the flow cell 10. Multiple library templates are hybridized, for example, to one of two types of amplification primers 47, 47' immobilized on the polymeric hydrogel 42.

Cluster generation may then be performed. In one example of cluster generation, the library templates are copied from the hybridized primers by 3' extension using a high-fidelity DNA polymerase 82. The original library templates are denatured, leaving the copies immobilized on the polymeric hydrogel 42. Isothermal bridge amplification or some other form of amplification may be used to amplify the immobilized copies. For example, the copied templates loop over to hybridize to an adjacent, complementary primer 47', 47 and a polymerase 82 copies the copied templates to form double stranded bridges, which are denatured to form two single stranded strands. These two strands loop over and hybridize to adjacent, complementary primers 47, 47' and are extended again to form two new double stranded loops. The process is repeated on each template copy by cycles of isothermal denaturation and amplification to create dense clonal clusters. Each cluster of double stranded bridges is denatured. In an example using the primers 47, 47', the reverse strand is removed by specific base cleavage, leaving forward template strands. While a single template strand 90 is shown in FIG. 6, clustering results in the formation of several template strands 90 immobilized on the polymeric hydrogel 42. This example of clustering is referred to as bridge amplification, and is one example of the amplification that may be performed. It is to be understood that other amplification techniques may be used, such as the exclusion amplification (Examp) workflow (Illumina Inc.).

A sequencing primer 92 may then be introduced that hybridizes to a complementary portion of the sequence of the template strand 90. This sequencing primer 92 renders the template strand 90 ready for sequencing using an incorporation mix.

The incorporation mix may include a plurality of fully functional nucleotides 80, the polymerase 82, and a liquid carrier. The liquid carrier of the incorporation mix may be water and/or an ionic salt buffer fluid, such as saline citrate at millimolar to molar concentrations, sodium chloride, potassium chloride, phosphate buffered saline, etc., and other buffers, such as tris(hydroxymethyl)aminomethane (TRIS) or (4-(2-hydroxyethyl)-1-piperazine ethanesulfonic acid) (HEPES). The liquid carrier may also include catalytic metal(s) intended for the incorporation reaction, such as $Mg^{2+}$, $Mn^{2+}$, $Ca^{2+}$, etc. A single catalytic metal or a combination of catalytic metals may be used, and the total amount may range from about 0.01 mM to about 100 mM.

The fully functional nucleotide 80 (FFN 80) includes the nucleotide, a 3' OH blocking group attached to the sugar of the nucleotide, and a fluorophore 84 attached to the base of the nucleotide. The nucleotide of the FFN 80 may be any nucleotide describe herein.

The nucleotide of the FFN 80 also includes a 3' OH blocking group attached thereto. The 3' OH blocking group may be linked to the 3' oxygen atom of the sugar molecule in the nucleotide. The 3' OH blocking group may be a reversible terminator that allows only a single-base incorporation to occur in each sequencing cycle. The reversible terminator stops additional bases from being incorporated into a nascent strand 94 that is complementary to the template strand 90. This enables the detection and identification of a single incorporated base. The 3' OH blocking group can subsequently be removed, enabling additional sequencing cycles to take place at each template strand 90. Examples of different 3' OH blocking groups include a 3'-$ONH_2$ reversible terminator, a 3'-O-allyl reversible terminator (i.e., $—CH{=}CHCH_2$), and 3'-O-azidomethyl reversible terminator (i.e., $—CH_2N_3$). Other suitable reversible terminators include o-nitrobenzyl ethers, alkyl o-nitrobenzyl carbonate, ester moieties, other allyl-moieties, acetals (e.g., tert-butoxy-ethoxy), MOM ($—CH_2OCH_3$) moieties, 2,4-dinitrobenzene sulfenyl, tetrahydrofuranyl ether, 3' phosphate, ethers, —F, $—H_2$, $—OCH_3$, $—N_3$, $—HCOCH_3$, and 2-nitrobenzene carbonate.

The nucleotide of the FFN 80 also includes a fluorophore 84 attached to the base of the nucleotide. The fluorophore 84 may be any optically detectable moiety, including luminescent, chemiluminescent, fluorescent, fluorogenic, chromophoric and/or chromogenic moieties. Some examples of suitable optically detectable moieties include fluorescein labels, rhodamine labels, cyanine labels (e.g., Cy3, Cy5, and the like), and the ALEXA® family of fluorescent dyes and other fluorescent and fluorogenic dyes.

The fluorophore 84 may be attached to the base of the nucleotide using any suitable linker molecule. In an example, the linker molecule is a spacer group of formula $—((CH_2)_2O)_n—$ wherein n is an integer between 2 and 50. The linker molecule includes a cleavage site (not shown in FIG. 6). When the cleavable linking molecule is used to attach the dark quencher 44, the cleaving chemistries for the cleavable linking molecule and for the linker molecule attaching the fluorophore 84 to the FFN 80 are orthogonal, so that removal of the FFN 80 after optical detection does not also remove the dark quencher 44.

In one example, the incorporation mix includes a mixture of different FFNs 80, which include different bases, e.g., A, T, G, C (as well as U or I). It may also be desirable to utilize a different type of fluorophore 84 for the different FFNs 80. For example, the fluorophores 84 may be selected so that each fluorophore 84 absorbs excitation radiation and/or emits fluorescence at a wavelength that is distinguishable from the other fluorophores 84. Such distinguishable analogs provide an ability to monitor the presence of different fluorophores 84 simultaneously in the same reaction mixture. In some examples, one of the four FFNs 80 in the incorporation mix may include no fluorophore 84, while the other three labeled FFNs 80 may include different fluorophore(s) 84.

Any polymerase 82 that can accept the fully functional nucleotide 80, and that can successfully incorporate the base of the fully functional nucleotide 80 into a nascent strand along the template strand 90 may be used. Example polymerases include those polymerases from family A, such as Bsu Polymerase, Bst Polymerase, Taq Polymerase, T7 Polymerase, and many others; polymerases from families B and B2, such as Phi29 polymerase and other highly processive polymerases (family B2), Pfu Polymerase (family B), KOD Polymerase (family B), 9oN (family B), and many others; polymerases from family C, such as *Escherichia coli* DNA Pol III, and many others, polymerases from family D, such as *Pyrococcus furiosus* DNA Pol II, and many others; polymerases from family X, such as DNA Pol μ, DNA Pol β, DNA Pol σ, and many others.

In this example method, any example of the incorporation mix is introduced into the flow cell 10, e.g., via the inlet. When the incorporation mix is introduced into the flow cell 10, the mix enters the flow channel 12, and contacts the surface chemistry where the template strands 90 are present.

The incorporation mix is allowed to incubate in the flow cell 10, and FFNs 80 are incorporated by a polymerase 82 into a nascent strand 94 generated along the template strand 90. As shown in FIG. 6, during incorporation, one of FFNs 80 is incorporated, by a respective polymerase 82, into one nascent strand 94 that extends one sequencing primer 92 and that is complementary to one of the template strands 90. Incorporation is performed in a template strand dependent fashion, and thus detection of the order and type of FFNs 80 added to the nascent strand 94 can be used to determine the sequence of the template strand 90. Incorporation occurs in at least some of the template strands 90 across the depressions 40 (or pads 48 of lane 50) during a single sequencing cycle. As such, in at least some of the template strands 90 across the flow cell 10, respective polymerases 82 extend the hybridized sequencing primer 92 by one of the FFNs 80 in the incorporation mix.

The incorporated FFNs 80 include the reversible termination property due to the presence of the 3' OH blocking group, which terminates further sequencing primer extension on the nascent strand 94 once the FFN 80 has been added.

After a desired time for incubation and incorporation, the incorporation mix, including at least some non-incorporated FFNs 80, may be removed from the flow cell 10 during a wash cycle. The wash cycle may involve a flow-through technique, where a washing solution (e.g., buffer) is directed into, through, and then out of flow channel 12, e.g., by a pump or other suitable mechanism.

Even after a wash cycle, some FFNs 80 may be non-specifically bound, as shown at reference numeral 80'. The non-specifically bound FFNs 80 do not get incorporated into a nascent strand 94, but become bound to the polymeric hydrogel 42 surface or are located in solution near the polymeric hydrogel 42 surface.

Without further incorporation taking place, the most recently incorporated FFNs 80 can be detected through an imaging event. During the imaging event, an illumination system (not shown) may provide an excitation light to the flow cell surfaces containing the surface chemistry. The fluorophore 84 of the incorporated FFNs 80 emit optical signals in response to the excitation light. The fluorophore 84 of the non-specifically bound FFNs 80' also emit optical signals in response to the excitation light. However, the signals of the non-specifically bound FFNs 80' may be quenched because the dark quenchers 44 are held within signal quenching proximity of the fluorophores 84 of non-specifically bound FFNs 80'. With a reduction in the signals from the non-specifically bound FFNs 80', the signal-to-noise ratio of the imaging event is improved.

After imaging is performed, a cleavage mix may then be introduced into the flow cell 10. In this example, the cleavage mix is capable of i) removing the 3' OH blocking group from the incorporated FFNs 80, and ii) cleaving the fluorophore 84 from the FFNs 80. Examples of 3' OH blocking groups and suitable de-blocking agents/components in the cleavage mix may include: ester moieties that can be removed by base hydrolysis; allyl-moieties that can be removed with NaI, chlorotrimethylsilane and $Na_2S_2O_3$, or with Hg(II) in acetone/water; azidomethyl which can be cleaved with phosphines, such as tris(2-carboxyethyl)phosphine (TCEP) or tri(hydroxypropyl)phosphine (THP); acetals, such as tert-butoxy-ethoxy which can be cleaved with acidic conditions; MOM ($—CH_2OCH_3$) moieties that can be cleaved with $LiBF_4$ and $CH_3CN/H_2O$; 2,4-dinitrobenzene sulfenyl, which can be cleaved with nucleophiles such as thiophenol and thiosulfate; tetrahydrofuranyl ether which can be cleaved with Ag(I) or Hg(II); and 3' phosphate which can be cleaved by phosphatase enzymes (e.g., polynucleotide kinase). Examples of suitable fluorophore cleaving agents/components in the cleavage mix may include: sodium periodate, which can cleave a vicinal diol; phosphines, such as tris(2-carboxyethyl)phosphine (TCEP) or tri(hydroxypropyl)phosphine (THP), which can cleave azidomethyl linkages; palladium and THP, which can cleave an allyl; bases, which can cleave ester moieties; or any other suitable cleaving agent.

Wash(es) may take place between the various fluid delivery steps. The sequencing cycle can then be repeated n times to extend the sequencing primer 92 by n nucleotides, thereby detecting a sequence of length n. In these examples, paired-end sequencing may be used, where the forward strands are sequenced and removed, and then reverse strands are constructed and sequenced.

Simultaneous paired end sequencing may be used with the primer sets 30A, 32A or 30B, 32B, or 30C, 32C, or 30D, 32D. With simultaneous paired end sequencing, during clustering, forward strands are generated on one region 42A, 42B of the polymeric hydrogel 42 and reverse strands are generated on the other region 42B, 42A of the polymeric hydrogel 42. Incorporation takes place simultaneously at the respective nascent strands 94 of the template strands 90 being sequenced at both regions 42A, 42B, and non-specifically bound FFNs 80' may be present at both regions 42A, 42B. In these examples, the signals of the non-specifically bound FFNs 80' may be quenched because respective dark quenchers 44 are held within signal quenching proximity of the fluorophores 84 of non-specifically bound FFNs 80' in each of the regions 42A, 42B. With a reduction in the signals from the non-specifically bound FFNs 80', the signal-to-noise ratio of the imaging event is improved.

Security Methods

The polymeric hydrogel 42 and dark quencher 44 disclosed herein may also be used as a security feature in a sensor that detects fluorescence. In this example method, the dark quencher 44 is attached to the polymeric hydrogel 42 via an example of the cleavable linking molecule disclosed herein. The length of the cleavable linking molecule is such that it can quench signals of FFNs 80 incorporated into nascent strands, or signals of other molecules of interest sequestered at the capture substance, thereby preventing the signals from being readily resolved. In these examples, a suitable cleaving agent of the cleavable linking molecule is added to the sensor in order to remove the dark quencher 44 before analysis can take place. Examples of suitable cleaving agents include TCEP for cleaving disulfides, ultraviolet light for photocleavable moieties such as PC biotin-PEG3-alkyne, or an enzyme for linkers such as BCN-PEG3-VC—PFP ester, or a protease for cleaving a peptide. This type of security feature could prevent flow cells 10 and other sensors from being used in equipment that is not specifically configured to be used with the flow cells 10 and other sensors.

As one example of the security feature, the cleavable linking molecule is a biotin-streptavidin binding pair. In this example, DBCO-S—S-PEG3-biotin may be attached to the polymeric hydrogel 42, and streptavidin may be attached to the dark quencher 44. The streptavidin also non-covalently attaches to the biotin. When the flow cell 10 is inserted into the sequencing system being used, the sequencing system determines whether the flow cell 10 is the appropriate flow cell 10 for the sequencing system. In an example, the flow cell 10 includes a bar code that is recognizable by the sequencing system. If the sequencing system recognizes the flow cell 10 as being proper, the system will prompt the user (e.g., via a user interface) to introduce the cleaving agent. In one example, formamide may be used to remove the streptavidin and the attached dark quencher 44. In another example, a reducing agent (e.g., TCEP, DTT, etc.) may be used to cleave the disulfide bond of the biotin, which also removes the streptavidin and the attached dark quencher 44. The flow cell 10 may then be exposed to a washing cycle and sequencing may be performed as described herein. If the sequencing system recognizes the flow cell 10 as being improper, the system will prompt the user (e.g., via a user interface) to remove the flow cell 10. If the user attempts to perform sequencing, the dark quencher 44 will suppress signals of the incorporated nucleotides.

As another example of the security feature, the cleavable linking molecule is cleavable biotin, such as DBCO-S—S-PEG3-biotin. In this example, the dark quencher 44 is attached to the biotin. When the flow cell 10 is inserted into the sequencing system being used, the sequencing system determines whether the flow cell 10 is the appropriate flow cell 10 for the sequencing system. If the sequencing system recognizes the flow cell 10 as being proper, the system will prompt the user (e.g., via a user interface) to introduce the cleaving agent. In this example, the reducing agent may be used to cleave the disulfide bond of the biotin linker. The flow cell 10 may then be exposed to a washing cycle and sequencing may be performed as described herein. If the sequencing system recognizes the flow cell 10 as being improper, the system will prompt the user (e.g., via a user interface) to remove the flow cell 10. If the user attempts to perform sequencing, the dark quencher will suppress signals of the incorporated nucleotides.

As still another example of the security feature, the cleavable linking molecule is an HP oligo modified with a cleavage site. In this example, the dark quencher 44 is attached to the free end of the HP oligo, which is also attached to the polymeric hydrogel 42. When the flow cell 10 is inserted into the sequencing system being used, the sequencing system determines whether the flow cell 10 is the appropriate flow cell 10 for the sequencing system. If the sequencing system recognizes the flow cell 10 as being proper, the system will prompt the user (e.g., via a user interface) to introduce the cleaving agent, which depends upon the cleavage site. The flow cell 10 may then be exposed to a washing cycle and sequencing may be performed as described herein. If the sequencing system recognizes the flow cell 10 as being improper, the system will prompt the user (e.g., via a user interface) to remove the flow cell 10. If the user attempts to perform sequencing, the temperature of sequencing (e.g., 60° C.) will denature the double stranded portion of the HP oligo, thus extending the HP oligo strand and placing the dark quencher 44 within signal quenching proximity of the nascent strand 94 to be generated. The dark quencher 44 will suppress signals of the incorporated nucleotides e.g., FFNs 80.

As yet another example of the security feature, the cleavable linking molecule is a DNA origami modified with a cleavage site. In this example, the dark quencher 44 is attached to the free end of the DNA origami, which is also attached to the polymeric hydrogel 42. When the flow cell 10 is inserted into the sequencing system being used, the sequencing system determines whether the flow cell 10 is the appropriate flow cell 10 for the sequencing system. If the sequencing system recognizes the flow cell 10 as being proper, the system will prompt the user (e.g., via a user interface) to introduce the cleaving agent, which depends upon the cleavage site. The flow cell 10 may then be exposed to a washing cycle and sequencing may be performed as described herein. If the sequencing system recognizes the flow cell 10 as being improper, the system will prompt the user (e.g., via a user interface) to remove the flow cell 10. If the user attempts to perform sequencing, the dark quencher will suppress signals of the incorporated nucleotides.

In examples of flow cells 10 where simultaneous paired end sequencing is performed, the dark quencher 44 may be attached to different regions 42A, 42B of the polymeric hydrogel 42 via an example of the cleavable linking molecule disclosed herein. In these examples, the dark quencher 44 may be used to suppress signals of molecules of interest in either the forward-read or the reverse-read direction. As mentioned, a suitable cleaving agent of the cleavable linking molecule (e.g., an acidic solution, formamide, a reducing agent, etc.) is added to the sensor in order to remove the dark quencher 44 before the signals in either direction can be readily resolved.

To further illustrate the present disclosure, examples are given herein. It is to be understood that these examples are provided for illustrative purposes and are not to be construed as limiting the scope of the present disclosure.

NON-LIMITING WORKING EXAMPLES

Example 1

A multi-layer structure with eight lanes was used in this example. The multi-layer structure included a fused silica and glass base support and a resin layer. Within each of the eight lanes, the resin layer was patterned with depressions, having a pitch of 550 nm and a diameter of 360 nm. A polymeric hydrogel, namely poly(N-(5-azidoacetamidyl-pentyl)acrylamide-co-acrylamide), was deposited in each of the lanes, and polishing was performed to remove the polymeric hydrogel from the interstitial regions and edge regions.

Seven of the lanes were grafted with different primers, as outlined in Table 1. Standard P5 and P7 primers were utilized, as well as modified P5 and P7 primers including dark quenchers.

TABLE 1

| Lanes | Primer(s) |
|---|---|
| 1 | P5 (see SEQ. ID. NO. 1) and P7 (see SEQ. ID. NO. 2) |
| 2 | P5 (see SEQ. ID. NO. 1) and P7 (see SEQ. ID. NO. 2) |
| 3 | P5 (see SEQ. ID. NO. 1) |
| 4 | AATGATACGGCGACCACCGAGAUCTAnAC (SEQ. ID. NO. 15) (i.e., Modified P5-1) where "n" is 4'-(2-nitro-4-toluyldiazo)-2'-methoxy-5'-methyl-azobenzene-4"-(N-ethyl)-N-ethyl-2-cyanoethyl-(N,N-diisopropyl)-phosphoramidite (commercially available as Black Hole Quencher-1® (BHQ-1) from TriLink BioTechnologies) |
| 5 | AATGATACGGCGACCACCGAGAUCTAnAC (SEQ. ID. NO. 16) (i.e., Modified P5-2) where "n" is 4'-(4-nitro-phenyldiazo)-2'-methoxy-5'-methoxy-azobenzene-4"-(N-ethyl)-N-ethyl-2-cyanoethyl-(N,N-diisopropyl)-phosphoramidite (commercially available as Black Hole Quencher-2® (BHQ-2) from TriLink BioTechnologies) |

TABLE 1-continued

| Lanes | Primer(s) |
|---|---|
| 6 | Modified P5-1 (see SEQ. ID. NO. 15) and P7 (see SEQ. ID. NO. 2) |
| 7 | Modified P5-2 (see SEQ. ID. NO. 16) and P7 (see SEQ. ID. NO. 2) |

Standard alkaline or carbonate buffer grafting conditions were used to load the appropriate primers into the lanes as set forth in Table 1.

Figure 7A:
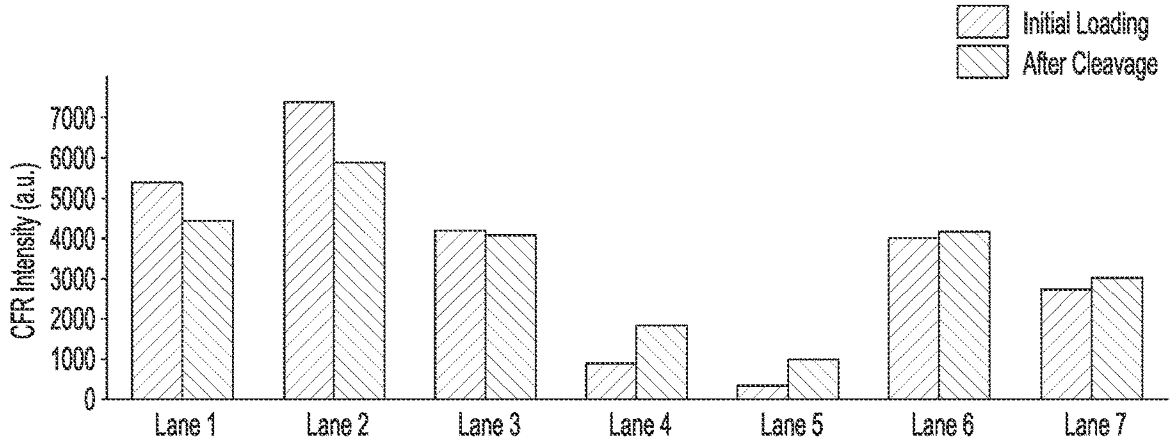
FIG. 7A and FIG. 7B are bar graphs that together illustrate the effect(s) of a dark quencher on local emissions of fluorescence within depressions of a sequencing flow cell at a pitch of 500 nm.

A CAL FLUOR® Red (CFR) assay was then performed to establish the baseline primer loading in each of the lanes of the flow cell. During the CFR assay, all lanes of the flow cell were exposed to fluorescently tagged (CAL FLUOR® Red (CFR) dye) oligonucleotides in a buffer solution. These oligonucleotides were complementary to the initially grafted P5, P7, or modified P5 primers. The fluorescently tagged complementary oligonucleotides bonded to the surface bound primers and excess CFR tagged complementary oligonucleotides were washed off. The surface was then scanned in a fluorescent detector to measure CFR intensity on the surface. The intensity within each lane after the initial grafting is shown in FIG. 7A. The intensity values for lanes 1, 2, and 3 (including the standard primers) were within the expected ranges for the primer concentrations used. The intensity values for lanes 4 and S demonstrated that Modified PS-1 and Modified P5-2, respectively containing the BHQ-1 or BHQ-2 species, displayed decreased CFR intensity (i.e., suppressed emission). The intensity values for lanes 6 and 7 demonstrated that the CFR tagged oligonucleotides hybridized to the standard P7 primers were detected even though the Modified P5-1 or Modified P5-2 primers were present.

The fluorescently tagged complementary oligonucleotides were then denatured from the surface primers. A cleavage mixture including the USER™ enzyme, which is a mixture of uracil DNA glycosylase (UDG) and the DNA glycosylase-lyase Endonuclease VIII, was introduced into each of the seven lanes. The cleavage mixture was allowed to incubate for about 30 minutes at 38° C. and then was flushed from each of the lanes with a mild citrate buffer (pH 7).

A second CAL FLUOR® Red (CFR) assay was then performed to determine the effect of the removal of the BHQ-1 or BHQ-2 species. The surface was then scanned in a fluorescent detector to measure CFR intensity on the surface. The intensity within each lane after dark quencher removal and additional grafting is also shown in FIG. 7A. The second intensity values (after dark quencher removal and additional grafting) for lanes 1, 2, and 3 (including the standard primers) were also within the expected ranges for the primer concentrations used. The second intensity values (after dark quencher removal and additional grafting) for lanes 4 and 5 demonstrated that removal of the Modified P5-1 and Modified P5-2, respectively containing the BHQ-1 or BHQ-2 species, resulted in an appreciable increase (100-150%) in the emission intensity measured. The second intensity values (after dark quencher removal and additional grafting) for lanes 6 and 7 were similar to the intensity values for these respective lanes after initial grafting, due, at least in part, to the fact that the hybridization of the CFR tagged complementary oligonucleotides can take place with approximately equivalent efficiency for the P7 strand and the slightly shorter Modified P5-1 and Modified P5-2 after dark quencher removal.

Figure 7B:
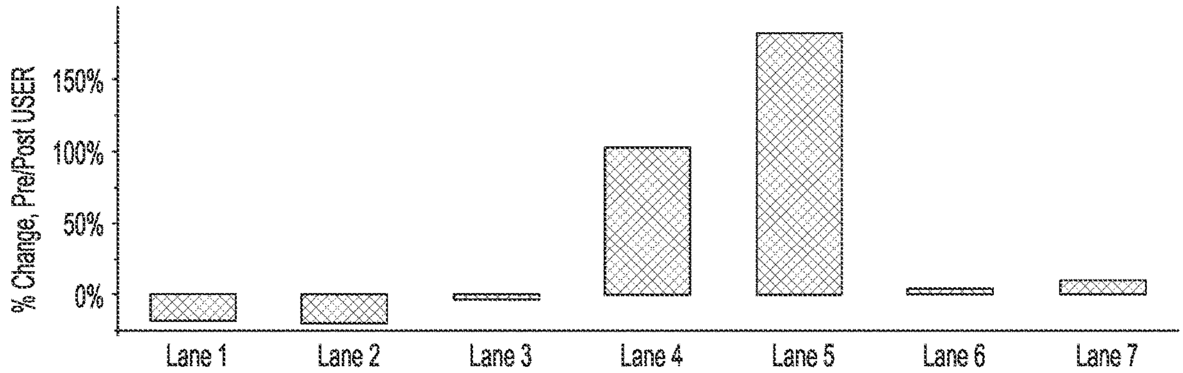

The change in emission was calculated between the CAL FLUOR® Red (CFR) assays, and the results are shown in FIG. 7B. The % change in emission in lanes 4 and 5 after dark quencher removal is clear.

Overall, the results in this example illustrate the ability of Modified P5-1 and Modified P5-2 to contribute to the suppression of fluorescent emissions within a flow cell surface. The results also show that cleavage of the dark quenchers from the modified P5 strands may contribute to an increase in emission intensity.

Example 2

A multi-layer structure with eight lanes was used in this example. The multi-layer structure included a fused silica and glass base support and a resin layer. Within each of the eight lanes, the resin layer was patterned with depressions, having a pitch of 700 nm and a diameter of 360 nm. A polymeric hydrogel, namely poly(N-(5-azidoacetamidyl-pentyl)acrylamide-co-acrylamide), was deposited in each of the lanes, and polishing was performed to remove the polymeric hydrogel from the interstitial regions and edge regions.

Eight of the lanes were grafted with different primers, as outlined in Table 2. Standard P5 and P7 primers were utilized, as well as some modified P5 and P7 primers including dark quenchers and other modified P7 primers including ALEXA FLUOR® 647. The modified P7 primers were used to asses if there was any dye specificity for the quenching and if the position of the emission from this molecule would result in enhanced quenching.

TABLE 2

| Lanes | Primer(s) |
|---|---|
| 1 | P5 (see SEQ. ID. NO. 1) and P7 (see SEQ. ID. NO. 2) |
| 2 | Modified P5-1 (see SEQ. ID. NO. 15) and CAAGCAGAAGACGGCATACGAnATn (SEQ. ID. NO. 17) (Modified P7) where the first "n" is 8-oxoguanine and the second "n" is the dye ALEXA FLUOR® 647 (commercially available from ThermoFisher) |
| 3 | Modified P5-1 (see SEQ. ID. NO. 15) and P7 (see SEQ. ID. NO. 2) |
| 4 | Modified P5-2 (see SEQ. ID. NO. 16) and Modified P7 (see SEQ. ID. NO. 17) |
| 5 | Modified P5-2 (see SEQ. ID. NO. 16) and P7 (see SEQ. ID. NO. 2) |
| 6 | AATGATACGGCGACCACCGAGACTAnAC (SEQ. ID. NO. 18) (i.e., Modified P5-3) where "n" is 4'-(2-nitro-4-toluyldiazo)-2'-methoxy-5'-methyl-azobenzene-4"-(N-ethyl)-N-ethyl-2-cyanoethyl-(N,N-diisopropyl)-phosphoramidite (commercially available as Black Hole Quencher-1® |

TABLE 2-continued

| Lanes | Primer(s) |
|---|---|
| | (BHQ-1) from TriLink BioTechnologies) and Modified P7 (see SEQ. ID. NO. 17) |
| 7 | Modified P5-3 (SEQ. ID. NO. 18) and P7 (see SEQ. ID. NO. 2) |
| 8 | AATGATACGGCGACCACCGAGACTAnAC (SEQ. ID. NO. 19) (i.e., Modified P5-4) where "n" is 4'-(4-nitro-phenyldiazo)-2'-methoxy-5'-methoxy-azobenzene-4"-(N-ethyl)-N-ethyl-2-cyanoethyl-(N,N-diisopropyl)-phosphoramidite (commercially available as Black Hole Quencher-2® (BHQ-2) from TriLink BioTechnologies) and P7 (see SEQ. ID. NO. 2) |

Standard alkaline or carbonate buffer grafting conditions were used to load the appropriate primers into the lanes as set forth in Table 2.

Figure 8A:
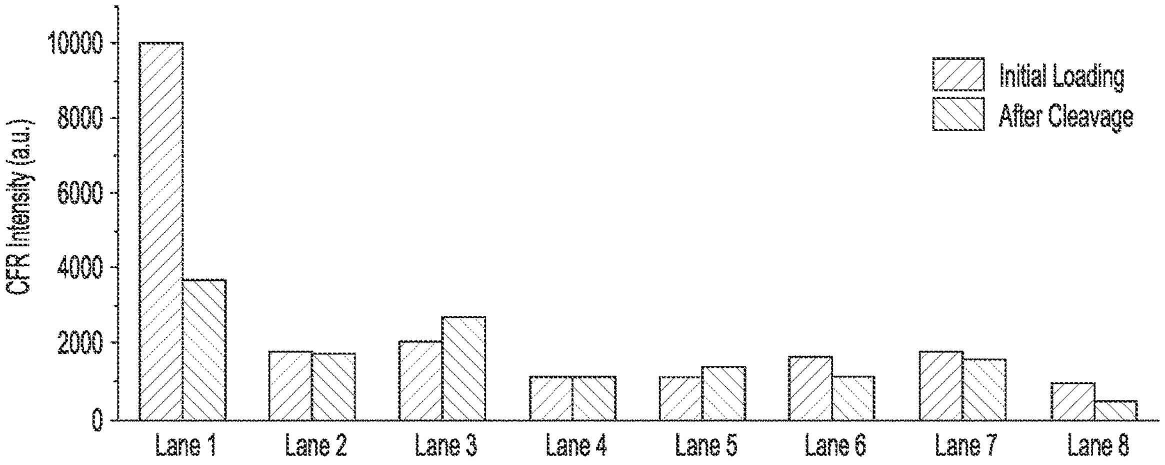
FIG. 8A and FIG. 8B are bar graphs that together illustrate the effect(s) of a dark quencher on local emissions of fluorescence within depressions of a sequencing flow cell at a pitch of 700 nm.

A CAL FLUOR® Red (CFR) assay was then performed to establish the baseline primer loading in each of the lanes of the flow cell. During the CFR assay, all lanes of the flow cell were exposed to fluorescently tagged (CAL FLUOR® Red (CFR) dye) oligonucleotides in a buffer solution. These oligonucleotides were complementary to the initially grafted P5 primers, P7 primers, modified P5 primers, or modified P7 primers. The fluorescently tagged complementary oligonucleotides bonded to the surface bound primers and excess CFR tagged complementary oligonucleotides were washed off. The surface was then scanned in a fluorescent detector to measure CFR intensity on the surface. The intensity within each lane after the initial grafting is shown in FIG. 8A. The intensity values for lane 1 (including the standard primers) were within the expected range for the primer concentrations used. The intensity values for lanes 2 through 8 demonstrated that Modified P5-1, Modified P5-2, Modified P5-3, and Modified P5-4 displayed decreased CFR intensity (i.e., suppressed emission).

The fluorescently tagged complementary oligonucleotides were then denatured from the surface primers. A cleavage mixture including the USER™ enzyme, which is a mixture of uracil DNA glycosylase (UDG) and the DNA glycosylase-lyase Endonuclease VIII, was introduced into each of the eight lanes. The cleavage mixture was allowed to incubate for about 30 minutes at 38° C. and then was flushed from each of the lanes with a mild citrate buffer (pH 7).

A second CAL FLUOR® Red (CFR) assay was then performed to determine the effect of the removal of the BHQ-1 or BHQ-2 species. The surface was then scanned in a fluorescent detector to measure CFR intensity on the surface. The intensity within each lane after dark quencher removal and additional grafting is also shown in FIG. 8A. The second intensity values (after dark quencher removal and additional grafting) for lane 1 (including the standard primers) was lower than expected, potentially, due to reduced P5 hybridization efficiency. The second intensity values (after cleavage) for lanes 3 and 5 demonstrated that removal of the Modified P5-1 and Modified P5-2, respectively containing the BHQ-1 or BHQ-2 species, resulted in an appreciable increase (20-30%) in the emission intensity measured. The second intensity values (after dark quencher removal and additional grafting) for lanes 2, 4, and 6 (with Modified P7) were slightly lower than the intensity values for these respective lanes after initial grafting. It is believed that the fluorophore-labeled P7 may have reduced the efficiency of the cleavage mix or the efficiency of the emission from the CAL FLUOR® Red fluorophore. The second intensity values (after dark quencher removal and additional grafting) for lanes 7 and 8, where the BHQ-1 or BHQ-2 species were not cleaved, were slightly lower than the initial intensity.

Figure 8B:
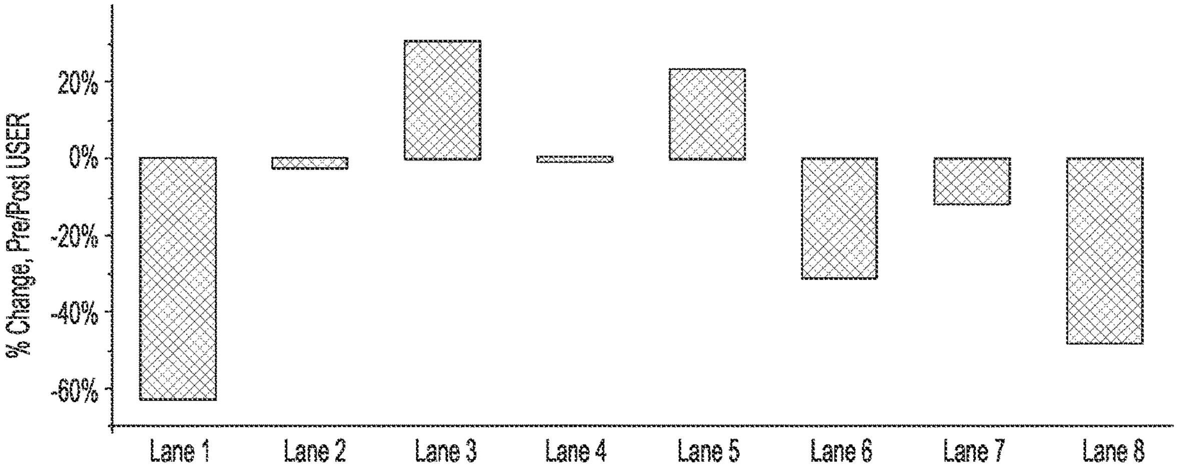

The change in emission was calculated between the CAL FLUOR® Red (CFR) assays, and the results are shown in FIG. 8B. The change in emission in lanes 3 and 5 after dark quencher removal is clear.

Overall, the results in this example illustrate the ability of Modified P5-1, Modified P5-2, Modified P5-3, and Modified P5-4 to contribute to the suppression of fluorescent emissions within a flow cell surface. The results also show that cleavage of the dark quenchers from some of the modified P5 strands may contribute to an increase in emission intensity.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A flow cell, comprising:

a substrate having a surface, the substrate consisting of i) a first material selected from the group consisting of epoxy siloxane, glass, acrylic, polystyrene, polypropylene, polyethylene, polybutylene, polyurethanes, polytetrafluoroethylene, a cyclic olefin/cyclo-olefin polymer, a polyimide, a polyamides, silica, fused silica, aluminum silicate, silicon, boron doped p+ silicon, silicon nitride, silicon oxide, tantalum pentoxide, hafnium oxide, carbon, and a metal, or ii) a multi-layered structure consisting of a base support and a resin over the base support, wherein the base support consists of a second material selected from the group consisting of epoxy siloxane, glass, acrylic, polystyrene, polypropylene, polyethylene, polybutylene, polyurethanes, polytetrafluoroethylene, a cyclic olefin/cyclo-olefin polymer, a polyimide, a polyamides, silica, fused silica, aluminum silicate, silicon, boron doped p+ silicon, silicon nitride, silicon oxide, tantalum pentoxide, hafnium oxide, carbon, and a metal, and wherein the resin is selected from the group consisting of an inorganic oxide, a polyhedral oligomeric silsesquioxane resin, an epoxy resin not based on a polyhedral oligomeric silsesquioxane, a poly(ethylene glycol) resin, a polyether resin, an acrylic resin, an acrylate resin, a methacrylate resin, and an amorphous fluoropolymer resin;

a plurality of depressions or a lane defined in the surface; and surface chemistry introduced in each of the plurality of depressions or in the lane, the surface chemistry including:

a polymeric hydrogel attached to the substrate surface in each of the plurality of depressions or in the lane, the polymeric hydrogel including a dark quencher that is configured to quench a signal that is within 4 nm or less of its position; and at least one primer set attached to the polymeric hydrogel.

2. The flow cell as defined in claim 1, wherein the polymeric hydrogel includes an acrylamide copolymer.

3. The flow cell as defined in claim 1, wherein the dark quencher is selected from the group consisting of dimethylaminoazobenzenesulfonic acid, 4'-(2-nitro-4-toluyldiazo)-2'-methoxy-5'-methyl-azobenzene-4"-(N-ethyl)-N-ethyl-2-cyanoethyl-(N,N-diisopropyl)-phosphoramidite, 4'-(4-nitrophenyldiazo)-2'-methoxy-5'-methoxy-azobenzene-4"-(N-ethyl)-N-ethyl-2-cyanoethyl-(N,N-diisopropyl)-phosphoramidite, 5'-Dimethoxytrityloxy-5-[(N-4"-carboxyethyl-4"-(N-ethyl)-4'-(2-Nitro-4-toluyldiazo)-2'-methoxy-5'-methyl-azobenzene)-aminohexyl-3-acrylimido]-2'-deoxyUridine-3'-[(2-cyanoethyl)-(N,N-diisopropyl)]-phosphoramidite, 5'-Dimethoxytrityloxy-5-[(N-4"-carboxyethyl-4"-(N-ethyl)-4'-(4-Nitro-phenyldiazo)-2'-methoxy-5'-methoxy-azobenzene)-aminohexyl-3-acrylimido]-2'-deoxyUridine-3'-[(2-cyanoethyl)-(N,N-diisopropyl)]-phosphoramidite, and combinations thereof.

4. The flow cell as defined in claim 1, wherein the polymeric hydrogel has the dark quencher removably attached through a cleavable linking molecule.

5. The flow cell as defined in claim 4, wherein the cleavable linking molecule includes a non-covalent binding pair.

6. The flow cell as defined in claim 5, wherein the dark quencher is present in an amount ranging from about 0.25 mol % to about 50 mol % relative to a total number of moles in the polymeric hydrogel.

7. The flow cell as defined in claim 1, wherein the polymeric hydrogel has the dark quencher incorporated into its backbone chain.

8. The flow cell as defined in claim 7, wherein the dark quencher is present in an amount ranging from about 0.25 mol % to about 50 mol % relative to a total number of moles in the polymeric hydrogel.

9. The flow cell as defined in claim 1, wherein the dark quencher is covalently attached to the polymeric hydrogel through a linking molecule.

10. The flow cell as defined in claim 9, wherein:

the linking molecule is a non-oligonucleotide linker; and the linking molecule is present in an amount ranging from about 0.25 mol % to about 50 mol % relative to a total number of moles in the polymeric hydrogel.

11. The flow cell as defined in claim 9, wherein:

the linking molecule is an oligonucleotide linker;

the polymeric hydrogel includes a plurality of a functional group that is to attach to the oligonucleotide linker; and the oligonucleotide linker is present in an amount sufficient to occupy from about 0.5% to about 50% of the plurality of the functional group.

12. The flow cell as defined in claim 1, wherein the dark quencher is attached to the polymeric hydrogel through a hairpin oligonucleotide or DNA origami.

13. The flow cell as defined in claim 1, wherein the dark quencher exhibits absorption at one or more wavelengths ranging from about 400 nm to about 670 nm.

14. The flow cell as defined in claim 1, wherein:

the substrate includes the plurality of depressions;

each depression of the plurality of depressions has a depth ranging from about 0.1 μm to about 100 μm;

each depression of the plurality of depressions has a diameter ranging from about 0.1 μm to about 100 μm; and an average pitch of the plurality of depressions is 500 nm or 700 nm.

15. A flow cell, comprising:

a substrate having a flat surface, the substrate consisting of i) a first material selected from the group consisting of epoxy siloxane, glass, acrylic, polystyrene, polypropylene, polyethylene, polybutylene, polyurethanes, polytetrafluoroethylene, a cyclic olefin/cyclo-olefin polymer, a polyimide, a polyamides, silica, fused silica, aluminum silicate, silicon, boron doped p+ silicon, silicon nitride, silicon oxide, tantalum pentoxide, hafnium oxide, carbon, and a metal, or ii) a multi-layered structure consisting of a base support and a resin over the base support, wherein the base support consists of a second material selected from the group consisting of epoxy siloxane, glass, acrylic, polystyrene, polypropylene, polyethylene, polybutylene, polyurethanes, polytetrafluoroethylene, a cyclic olefin/cyclo-olefin polymer, a polyimide, a polyamides, silica, fused silica, aluminum silicate, silicon, boron doped p+ silicon, silicon nitride, silicon oxide, tantalum pentoxide, hafnium oxide, carbon, and a metal, and wherein the resin is selected from the group consisting of an inorganic oxide, a polyhedral oligomeric silsesquioxane resin, an epoxy resin not based on a polyhedral oligomeric silsesquioxane, a poly(ethylene glycol) resin, a polyether resin, an acrylic resin, an acrylate resin, a methacrylate resin, and an amorphous fluoropolymer resin;

surface chemistry introduced on the flat surface such that it appears to protrude from the flat surface, the surface chemistry including:

a polymeric hydrogel applied to the substrate surface as a plurality of pads, wherein each of the plurality of pads is isolated from each other of the plurality of pads by interstitial regions, the polymeric hydrogel including a dark quencher; and at least one primer set attached to the polymeric hydrogel.

16. The flow cell as defined in claim 15, wherein the dark quencher is configured to quench a signal that is within 4 nm or less of its position.

* * * * *